United States Patent [19]

Tedder et al.

[11] Patent Number: 5,776,775
[45] Date of Patent: Jul. 7, 1998

[54] ANTI-LAM 1-3 ANTIBODY AND HYBRIDOMA

[75] Inventors: Thomas F. Tedder, Wellesley; Olivier G. Spertini, Newton, both of Mass.

[73] Assignee: Dana-Farber Cancer Institute, Boston, Mass.

[21] Appl. No.: 215,366

[22] Filed: Mar. 21, 1994

Related U.S. Application Data

[63] Continuation of Ser. No. 720,602, Jun. 25, 1991, abandoned, which is a continuation-in-part of Ser. No. 313,109, Feb. 21, 1989, abandoned.

[51] Int. Cl.$^6$ .................. C07K 16/18; C07K 16/28; C12N 5/12

[52] U.S. Cl. ............. 435/343.2; 435/326; 435/332; 435/334; 435/343; 530/387.1; 530/387.3; 530/388.1; 530/388.22; 530/388.7; 530/388.73; 530/388.75; 530/391.3

[58] Field of Search ............. 424/130.1, 134.1, 424/139.1, 141.1, 143.1, 144.1, 153.1, 154.1; 435/70.21, 240.27, 172.2, 325, 326, 334, 343.2; 530/387.1, 387.3, 388.1, 388.73, 388.75, 388.7, 388.2

[56] References Cited

U.S. PATENT DOCUMENTS 5,098,833  3/1992  Lasky ........................... 435/69.1

FOREIGN PATENT DOCUMENTS 0386906  9/1990  European Pat. Off. .

OTHER PUBLICATIONS

L. Flaherty et al., "A monoclonal antibody (MAb) to L-selectin does not prevent neutrophil (PMN) emigration into an inflamed peritoneal cavity," The Faseb Journal USA 6: p. A1889.
Harris et al. Tibtech 11:42–45 (1993).
Ward Therapeutic Immunol. 1:165–171 (1994).
Reinhen F et al J. Immunol. 128:463–468 1982.
Tedder et al. J Immunol. 144:532–540 (1990).
Gatenby et al. J. Immunol 129:1997–2000 (1982).
Kishimoto et al. PNAS 87:2244–2248 (1990).
Spertini et al. J Immunol. 147:942–949 (1991).
Bowen et al. J. Cell Biol. 109:421–427 (1989).
Tedder et al. J. Exp Med 170:123–133 (1989).
Wu et al. J Cell Biol 107:1845–1851 (1988).
Morrison Science 229:1202–1207 (1985).

*Primary Examiner*—Lila Feisee
*Assistant Examiner*—Phillip Gambel
*Attorney, Agent, or Firm*—White & Case

[57] ABSTRACT

A hybridoma cell line produced by the fusion of NS-1 myeloma cells with spleen cells obtained from mice immunized with Leukocyte Adhesion Molecule-1 (LAM-1) cDNA transfected cells. The cell line produces a monoclonal antibody reactive with human, monkey, cow, rabbit, sheep, dog, cat, pig and goat LAM-1. The monoclonal antibody produced by the cell line, anti-LAM1-3, may be clinically useful in blocking leukocyte entry into sites of inflammation or tissue injury.

5 Claims, 11 Drawing Sheets

FIG. 3A

```
              300                      310                        320
  T   S   A   C   T   F   I   C   S   E   G   T   E   L   I   G   K   K   K   T   I   C   E   S   S   G   I   W
ACC TCT GCA TGT ACC TTC ATC TGC TCA GAA GGA ACT GAG TTA ATT GGG AAG AAA ACC ATT TGT GAA TCA TCT GGA ATC TGG  1018
                330                      340                                       350
  S   N   P   S   P   I   C   Q   K   L   D   K   S   F   S   M   I   K   E   G   D   Y   N   P   L   F   P
TCA AAT CCT AGT CCA ATA TGT CAA AAA TTG GAC AAA AGT TTC TCA ATG ATT AAG GAG GGT GAT TAT AAC CCC CTC ATT CCA  1102
                                                               370
  V   A   V   M   V   T   A   F   S   G   L   A   F   I   W   L   A   R   R   L   K   K   G   K   K   S   K
GTG GCA GTC ATG GTT ACT GCA TTC TCT GGG TTG GCA TTT ATC ATT TGG CTG GCA AGG AGA TTA AAA AAA GGC AAG AAA TCC AAG  1186
  380
  R   S   M   N   D   P   Y   *
AGA AGT ATG AAT GAC CCA TAT TAA ATCGCCCTTG GTGAAAGAAA ATTCTTGGAA TACTAAAAAT CATGAGATCC TTTAAATCCT TCCATGAAAC  1280
GTTTGTGTG GTGGCACCTC CTACGTCAAA CATGAAGTGT GTTCCTTCA GTGCATCTGG GAAGATTTCT ACCTGACCAA CAGTTCCTTC AGCTTCCATT  1380
TCACCCCTCA TTTATCCCTC AACCCCCAGC CCACAGGTGT TTGCTCTTC CAGCTTTTG TCTTTTCTGA GGAGAAACAA ATAAGACCAT AAAGGAAAG  1480
GATTCATGTG GAATATAAAG ATGGCTGACT GTGAATATGG ACTCAGTTT CAATTCAGTG CTGTACTTGA TGACAGACAC GGTACACTCT ATGAAGTCAA  1580
AGTGCAAATT TGATACATAT AGTAAGAAAA TGCTCTCCT TTCTAACTCC AGTGAAGTAA CTCGTCTCTG TATACGTGGA AGCCTCGCCG TCTGTGAATT  1680
AAGTCTACGC TCTCCTTTCT TTCTAACTCC CTTCAGCCTC CCCACCTTCA AGAGTCCTA GTTGGCTGAC TTCCACACCT AGCATCTCAT GAGTGCCAAG  1780
GGACCATCCT ATTTAACTGG AAGAGAGAGA ATAGCCTGCG CTGTTTTTA GTTGGGGGT CCTTTATGA GACCCATTCC TATTTCTTAT AGTCAATGTT  1880
CAAAAGGAGA GAAGAGAGAA ATAGCCTGCG CTGTTTTTTA GTTGGGGGT CCTTTATGA CTCTTTGATG TCATATGGAA GAGTTAAAAC AGGTGGAGAA  1980
TCTTTTATCA CGATATTATT AGTAAGAAAA ATGCTCTCCT TTCCCTGCC CAACTGACTG TTATCCACTT ACCTAGATTC TACATATTCT TTAAATTTCA  2080
ATTCCTTGAT TCACAATGAA ATGCTCTCCT TTCCCTGCC CCAGACCTT AATCCAACCC ATGATGAGCT CCTAGATTC TACATATTCT TCTCAGGCCT  2180
CCCTCAACCC CACCACTTCT TTTAACTA GTCCTTTACT AATCCAACCC ATGATGAGCT CCTCTTCCTG GCTTCTTACT CCTGTAACAT  2280
GCAATTTGC ATTTGAATAA AGCCTGCTTT TTAAGTGTTA AAAAgaattc                                                      2330
```

|          |     |   |   |   |   |   |   |   |   |   |   |   |   |   |   |   |   |   |   |   |   |   |   |   |   |   |   |   |   |     |
|----------|-----|---|---|---|---|---|---|---|---|---|---|---|---|---|---|---|---|---|---|---|---|---|---|---|---|---|---|---|---|-----|
| LAM-1    | 173 | C | Q | P | – | – | W | S | C | S | G | H | G | E | C | V | E | I | I | N | – | Y | T | C | N | C | D | V | G | Y | Y | G | P | Q | C | Q | 205 |
| EGF      | 6   | C | P | L | S | H | D | G | Y | C | L | H | D | G | V | C | M | Y | I | E | A | L | D | K | Y | A | C | N | C | V | V | G | Y | I | G | E | R | C | Q | 43  |
| F-IX     | 51  | C | E | S | – | – | N | P | C | L | N | G | G | S | C | K | D | D | I | N | S | – | Y | E | C | W | C | P | F | G | F | E | G | K | N | C | E | 83  |
| F-PGPCP  | 382 | C | K | M | – | – | N | P | C | K | N | G | G | T | C | Y | P | T | E | T | S | – | Y | V | C | T | C | V | P | G | Y | S | G | D | Q | C | E | 414 |

ANTI-LAM 1-3 ANTIBODY AND HYBRIDOMA

RELATED APPLICATION

This application is a continuation of the U.S. application Ser. No. 07/720,602 filed Jun. 25, 1991, now abandoned which in turn is a continuation-in-part of application Ser. No. 07/313/109, filed Feb. 21, 1989 now abandoned.

GOVERNMENT SUPPORT

This invention was made with U.S. Government support and the U.S. Government has certain rights in this invention under PHS grants CA-34183 and AI-26872.

FIELD OF THE INVENTION

This invention relates to human lymphocyte associated cell surface proteins. Further, the herein invention relates particularly to a hybridoma cell line and a monoclonal antibody produced by said hybridoma cell line which is useful in detecting immunological disorders symptomatic of disease by identifying T and B cells, for instance, which have reduced LAM-1 expression.

This invention relates to a hybridoma cell line which produces a monoclonal antibody to a human Leukocyte-Adhesion Molecule-1 (LAM-1) [previously called lymphocyte-associated cell surface protein], and to the antibody produced by the cell line. The invention particularly relates to a cell line and a monoclonal antibody produced by the cell line which is useful in the identification and treatment of AIDS by identifying cells, such as, for example, T and B cells, which have reduced LAM-1 expression. Neutrophils can also down-regulate I..AM-1 expression following activation. Thus LA.14-1 can be a useful marker for identifying neutrophils [6]. For example, the antibody is useful in blocking leukocyte entry into sites of inflammation or tissue damage, and preventing kidney or other organ transplant rejection which is mediated by leukocytes.

BACKGROUND OF THE INVENTION

Genes exclusively expressed by one cell lineage, but not by another, often define the function of that cell population. The generation of genes by the assembly of functionally independent domains has occurred frequently as new genes have evolved to encode proteins with new functions. An inducible endothelial-leukocyte adhesion molecule (ELAM-1.) is expressed on the surface of cytokine—treated endothelial cells. This molecule is thought to be responsible for the accumulation of blood leukocytes at sites of inflammation by mediating the adhesion of cells to the vascular lining (Bevilacqua et al., Proc. Natl. Acad. Sci. USA 84: 9238 (1987)). A granule membrane protein found in platelets and endothelial cells, termed GMP-140, has been cloned and is homologous with ELAM-1 (Johnson et al., Blood Suppl. 71: 327a (1988)).

Applicant's co-pending application Ser. No. 07/313,109 describes a human cDNA sequence encoding the lymphocyte-associated cell surface protein LAM-1, hereafter redesignated the leukocyte-adhesion molecule-1 (LAM-1), which contains domains homologous with binding domains of animal lectins, growth factors, and C3/C4 binding proteins, and the LAM-1 protein encoded by the cDNA sequence. Antagonists to LAM-1 were used in a method of treating a human patient suffering from a lymphocyte-mobilizing condition which involves administering a therapeutic amount of the antagonist in a non-toxic pharmaceutical carrier.

Normal leukocytes have the ability to leave the circulation and localize in specific lymphoid organs or inflammatory sites through interactions between cell-surface receptors and ligands on endothelial cells [references 1–3, see Glossary]. The Leukocyte-Adhesion Molecule-I (LAM-1) contains an amino-terminal, lectin-like domain which may interact with specific glyco-conjugates expressed on high endothelial venules (HEV) of peripheral LN (lymph nodes) and activated endothelium [3–5]. LAM-1 is expressed by human peripheral lymphocytes, neutrophils, eosinophils, monocytes and hematopoietic progenitor cells [5–8]. LAM-1 is expressed by the majority of circulating lymphocytes and memory T cells, but is lost following several days of mitogen stimulation [5,9,10]. In contrast, LAM-1 is shed from the cell surface within minutes of exposure of lymphocytes and neutrophils to PMA [5,6,11]. Both lymphocytes and neutrophils express a single LAM-1 protein product, but the molecular weight (Mr) of cell-surface LAM-1 on lymphocytes is 74,000 and that of neutrophils is 90,000100,000 [6,9,12].

The specific adhesion of some tumor cells to the capillary endothelium and the existence of organ specific metastasis suggest that interactions between tumor cells and normal tissues influence tumor localization [13–15]. Although the molecules that mediate these events in malignant cells have not been completely described, many cell surface molecules involved in the adhesion and migration of normal leukocytes may be involved in the dissemination of hematopoietic malignant cells [1–3]. The mLHR has been implicated in the dissemination of lymphomas [14–16], and a calcium-dependent phosphomannosyl-binding site on human malignant lymphoblastoid cell lines mediates peripheral LN HEV binding [17]. In the invention described herein, the structure, function and regulation of LAM-1 expression was examined on normal lymphocytes and compared to LAM-1 of malignant leukocytes.

The LAM-1 molecule is a member of a new family of cellular adhesion/homing molecules that contain a lectin-like domain at their amino-terminal end followed by an epidermal growth factor-like domain and short consensus repeat units like those found in C3/C4 binding proteins. In J. Exp. Med., 170: 123–133 (1989) [4) and co-pending application Ser. No. 07/313,109, T. F. Tedder et al. report the isolation and chromosomal localization of cDNAs encoding the novel cell surface molecule LAM-1. In Eur. J. Immunol., 20: 1351–1355 (1990), T. F. Tedder et al. reported that human antigen-specific memory T cells express the LAM-1 necessary for lymphocyte recirculation. In J. Biological Chemistry, 265: 7760–7677 (1990), Ord et al. (under the auspices of T. F. Tedder) reported the structure of the gene encoding the LAM-1 of lymphocytes and neutrophils. In J. Immunology, 144: 532–542 (1990) [5], T. F. Tedder et al. described two monoclonal antibodies, LAM1-1 and LAM1-2, that react with LAM-1. [Note: As used herein, LAM-1 refers to the leukocyte-adhesion molecule-1 itself and "LAM1-X" refers to an antibody x which binds to an epitope of LAM-1.)

The monoclonal antibodies LAM1-1 and LAM1-2 were found to be reactive with the majority of blood lymphocytes, NK (Natural Killer) cells, neutrophils, monocytes and hematopoietic progenitor cells. Binding of LAM-1 may participate in the process of leukocyte extravasation into lymphoid organs or sites of acute inflammation with subsequent loss of LAM-1 from the cell surface. LAM-1 is also recognized by the TQI and Leu-8 monoclonal antibodies that have been previously identified.

The loss of LAM-1 expression after leukocyte activation in vivo, with the concomitant increase in expression of CD2, CD18, CD11a or CD11b may result in significant and dramatic increases in migration and ability to recognize endothelial cell surfaces. Of significance is the fact that patients with AIDs have diminished expression of LAM-1 on their T and B cells. This may also occur in other immunological syndromes. Therefore, alterations in LAM-1 expression by neutrophils are significant because the mLHR is involved in neutrophil migration into sites of acute inflammation. LAM-1, in conjunction with other selecting and receptors, is involved in the extravasation of most leukocytes. The expression of LAM-1 by different leukocytes sub-populations thus plays a key role in determining the characteristics and magnitude of local immune responses [5].

As lymphocyte migration and infiltration into areas of tissue damage or injury or tissue transplant can cause or increase pathology, agents that impede these processes can be used as an antigen to produce antibodies against this protein and to develop antagonistic ligands that can interfere with lymphocyte adhesions and function. The use of these reagents in research will permit the determination of the 3-dimensional structure of LAM-1 and clarify its role in lymphocyte function. The administration of these reagents to patients can be used to block or reduce pathology. As an example subpopulations of malignant cells that express this antigen would allow the receptor to function in metastasis of tumor cells. Agents developed to block receptor function can inhibit the metastasis and homing of malignant cells.

The present invention relates to the production of a new antibody to LAM-1. The new monoclonal antibody, anti-LAM1-3, is useful in radioisotope or immunofluorescent assays for the detection of LAM-1. For example, identifying species which have or do not have LAM-1. The antibody is further useful for separating cells expressing LAM-1 from cells not expressing LAM-1 or visa versa. Furthermore, this monoclonal antibody also completely blocks leukocyte attachment to HEV or endothelium.

Neutrophil-mediated inflammation is involved in a number of human clinical manifestations, including the adult respiratory distress syndrome, multi-organ failure and reperfusion injury. One way of inhibiting this type of inflammatory response would be to block competitively the adhesive interactions between neutrophils and the endothelium adjacent to the inflamed region. Anti-LAM1-3 reacts with LAM-1 on many animal species, but does not bind the mLHR. Anti-LAM1-3 blocks completely lymphocytic traffic to lymph nodes and extravasation of neutrophil$ from blood to inflammatory sites. The administration of soluble forms of anti-LAM1-3 could be clinically effective for the inhibition of neutrophil-mediated inflammation. Anti-LAM1-3 also blocks lymphocyte adhesion to human HEV and activated endothelium. Therefore, it is likely that the use of anti-LAM13 will block lymphocyte entry into sites of inflammation or tissue injury. Such activity will be useful for preventing kidney or other organ transplant rejection which is mediated by lymphocytes.

It is also within the scope of the invention to prepare chimerized monoclonal antibodies from the mouse antibodies. Antibodies are Y-shaped molecules consisting of two long "heavy" chains which define the stem and arms of the Y and two short "light" chains which are attached to the outside of the arms. The amino-terminal ends of the arms of the antibody molecule contain the variable regions of the antibody. The variable regions are specific for a particular antigen. The stem of the molecule is the "constant" region which ends in a carboxylate function (COO—) and remains the same from molecule to molecule in antibodies of the same isotype in the same species.

The constant region of the mouse antibody has been found to be the primary source human immune reactions to mouse monoclonal antibodies. Using standard genetic engineering techniques, mouse variable regions have been fused to human constant regions to generate "chimeric" (from chimera or chimaera, a monster of Greek mythology which had a lion's head, a goat's body and a serpent's tail) antibodies. These chimeric antibodies thus possess regions of different genetic origin and have been found to have a lower tenency to produce allergic reactions.

SUMMARY OF THE INVENTION

The invention generally features a human cDNA sequence encoding lymphocyte-associated cell surface protein LAM-1, which contains domains homologous with binding domains of animal lectins, growth factors, and C3/C4 binding proteins; and the LAM-1 protein encoded by the cDNA sequence or an immunogenic fragment of LAM-1. In a preferred embodiment, the cDNA sequence is isolated from a population of B cell—specific cDNAs from a human tonsil cDNA library, and the amino acid sequence of the protein is subsequently as indicated in FIG. 3, more preferably 80%, homologous with the sequence shown in FIG. 3 and most preferably 90% homologous. (Here "substantially as indicated" defines a sequence close enough to the indicated sequence to have the same function.)

A hybridoma cell line produced by the fusion of NS-1 myeloma cells with spleen cells obtained from mice immunized with LAM-1 cDNA-transfected 300.19 cells (a mouse pre-B cell line). The hybridoma cell line produces a monoclonal antibody reactive with human, monkey, cow, rabbit, sheep, dog, cat, pig and goat leukocyte adhesion molecule-1. LAM-1. The monoclonal antibody produced by the cell line of the claimed invention identified as anti-LAM1-3, may be clinically useful in blocking leukocyte entry into sites of inflammation or tissue injury.

In another respect, the invention features antibody developed against lymphocyte-associated cell surface protein LAM-1, or a fragment thereof, or against a molecule that specifically associates with LAM-1, or a fragment thereof, to generate a functional molecule.

In another aspect, the invention features a method of identifying cells that express LAM-1 which involves reacting the antibody just described with a population of cells and isolating those that bind the antibody. Binding of antibody can also be used to block the receptor activity of LAM-1.

In another aspect, the invention features a method of treating a human patient suffering from a lymphocyte—mobilizing condition which involves administering a therapeutic amount of an antagonist to LAM-1 in a non-toxic pharmaceutical carrier substance. In preferred embodiments of the method the patient is suffering from tissue damage, an autoimmune disorder, or cancer, or the patient is an organ or tissue transplant recipient.

In another aspect, the invention features using the cDNA sequence defined above to isolate cross-hybridizing human cDNAs.

In another aspect, the invention features using LAM-1 to identify a ligand which will bind to it or to a molecule that is specifically associated with LAM-1 to generate a functional molecule.

As used herein, the term antagonist includes any agent which interacts with LAM-1 and interferes with its function; e.g., antibody reactive with LAM-1 or any ligand which binds to LAM-1.

Lymphocyte-associated cell surface protein LAM-1 is a unique receptor protein which has not previously been identified. LAM-1 contains domains that are homologous with those found in several different receptors and is a newly described member of a gene family that includes ELAM-1 and GMP-140, proteins which have been implicated in cell adhesion. LAM-1 most likely serves a similar function but is uniquely expressed by lymphocytes. The isolation of cDNA encoding LAM-1 has allowed the determination of the structure of this molecule; the cDNA has been used to transfer expression of LAM-1 to cells that do not express this gene.

Antibodies reactive with LAM-1 can be used to identify cells that express this receptor and to block its function. In addition, the cDNA protein product can be used to develop antagonistic ligands that can interfere with lymphocyte adhesion and function, and thereby be used to treat such conditions as tissue damage and metastasis of cancer cells.

Other features and advantages of the invention will be apparent from the following description of the preferred embodiments thereof and from the claims.

BRIEF DESCRIPTION OF THE DRAWINGS

In the drawings.

FIG. 3 shows the determined cDNA nucleotide sequence and the deduced amino acid sequence of LAM-1;

FIGS. 4, 4B and 4C show the homologies of LAM-1 and other proteins;

STATEMENT OF DEPOSIT

A hybrid cell line which produces the anti-LAM-1 monoclonal antibody anti-LAM1-3 embodying this invention has been deposited with the American Type Culture Collection, 12301 Parklawn Drive, Rockville, Md. 20852 on Jun. 12, 1991 and is assigned A.T.C.C. Deposit No. HB 10771.

DETAILED DESCRIPTION OF THE INVENTION

B cell-specific cDNAs were isolated from a human tonsil cDNA library (ATCC No. 37546) using differential hybridization with labelled cDNAs derived from either B cell (RAJI) RNA or T cell (HSB-2) RNA (Tedder et al., Proc. Natl. Acad. Sci. USA, 85: 208–212 (1988)). Positive plaques were isolated and cloned, and the cDNA inserts were subcloned into the plasmid pSP65 (Promega, Madison, Wis.). Nucleotide sequences were determined using the method of Maxam and Gilbert (Meth. Enzymol., 65: 499 (1980)). Gap penalties of −1 were assessed during homology analysis for each nucleotide or amino acid in the sequence where a gap or deletion occurred. One of the 261 RAJI+ HSB2− cDNA clones isolated, B125, contained a 1.90 kb cDNA insert that hybridized with a 2.4 kb RNA species found in several B cell lines (Tedder et al., supra). However, B125 did not hybridize with any of the other RAJI+ HSB2− clones or with mRNA from several T cell lines. The B125 cDNA clone was characterized by restriction mapping and nucleotide sequence determination. A near-full-length 2.3 kb cDNA that hybridized with B125 was isolated, sequenced, and termed pLAM-1.

Figure 1:
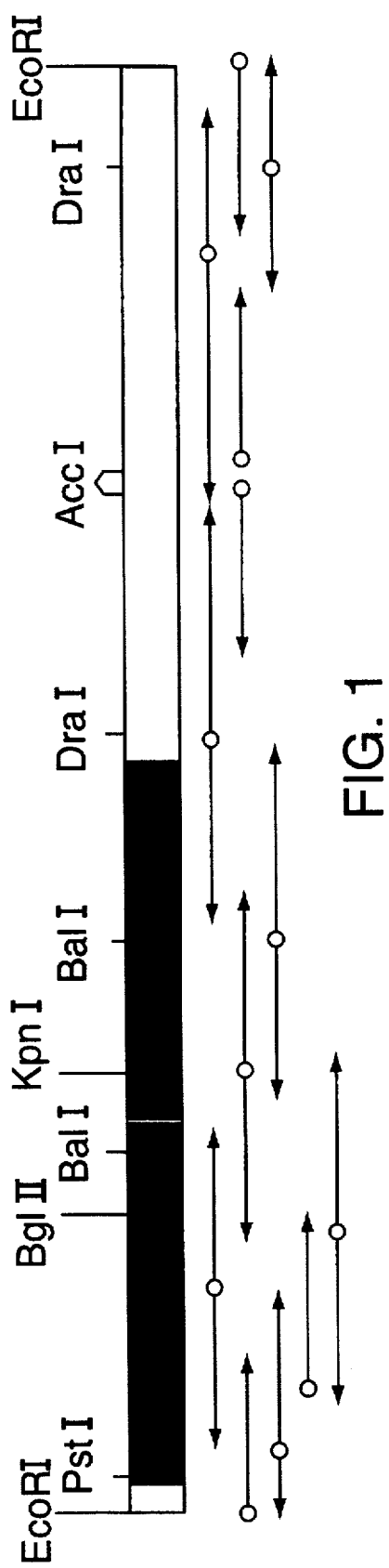
FIGS. 1 and 2 show the structure of the LAM-1 cDNA clone.

As shown in FIG. 1, a restriction map was constructed by the standard single, double or triple digestions of pLAM-1. The putative coding region is shown in black. Arrows indicate the direction and extent of nucleotide sequence determination and the open circles indicate 51-end labeling. In FIG. 1B, a schematic model of the structure of the LAM-1 mRNA is shown. Thin lines indicate 51 and 31 untranslated sequences (UT), while the thick bar indicates the translated region. The boxes represent the lectin-like and epidermal growth factor (EGF)-like domains and the two short consensus repeat (SCR) units. The open box indicates the putative transmembrane (TM) region.

The expression of LAM-1 mRNA by cell lines of lymphoid and non-lymphoid origin was examined. Northern Blot analysis revealed that LAM-1 hybridized strongly to a 2.6 kb RNA species and weakly to a 1.7 kb RNA species in poly(A)+ RNA isolated from the B cell lines RAJI, SB, Laz-509 and GK-5. However, RNA isolated from two pre-B cell lines (Nalm-6 and PB-697), three B cell lines (Namalwa, Daudi and BJAB), a myelomonocytic cell line (U937 and U937 cultured with LPS) and an erythroleukemic (K-562) cell line did not hybridize with LAM-1, suggesting that expression of this gene was preferentially associated with B lymphocytes.

Figure 3A:
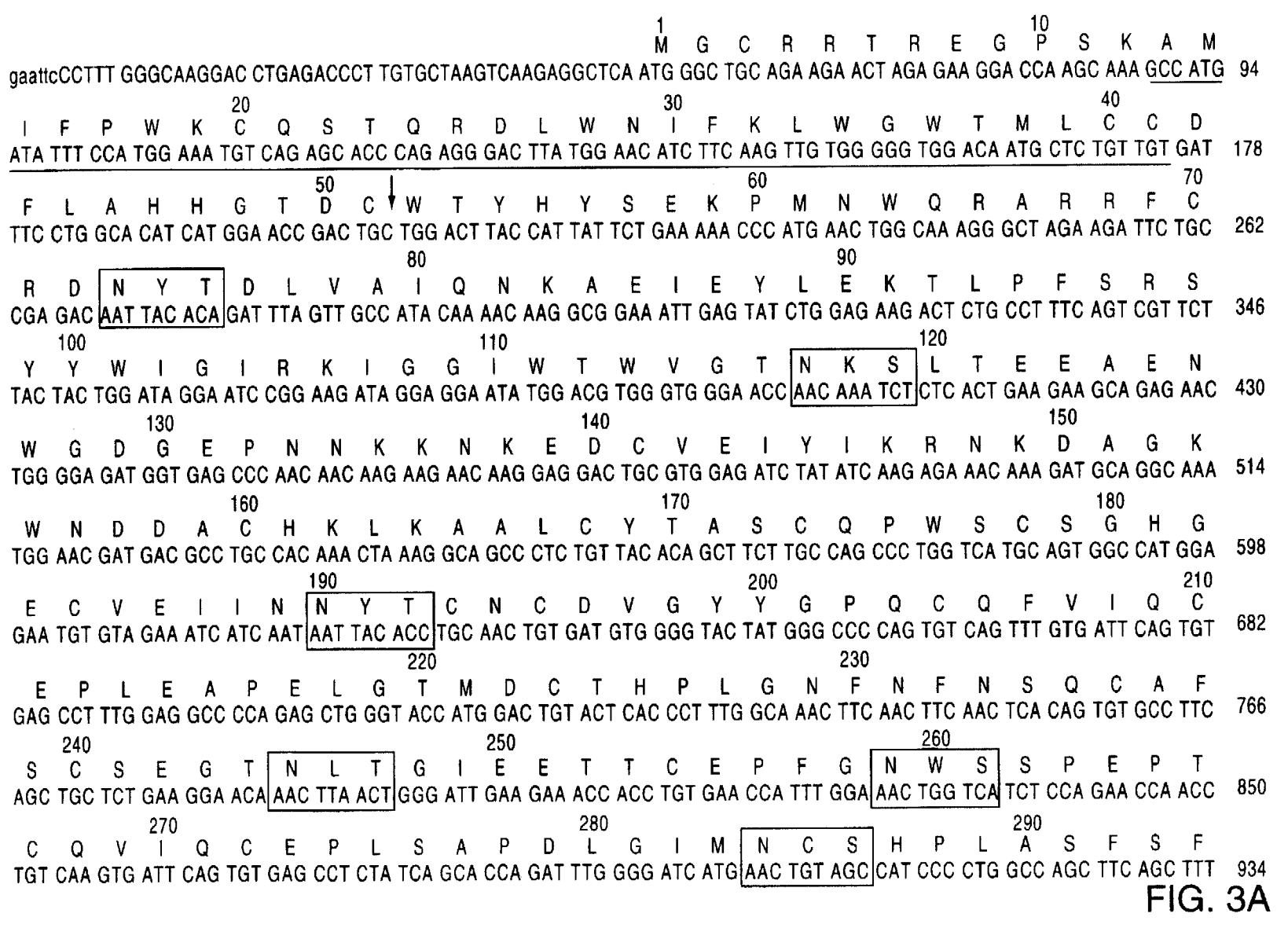

The B125 cDNA clone contained a 1,181 bp open reading frame that could encode a protein of 372 amino acids as shown in FIG. 3. The numbers shown above the amino acid sequence designate amino acid residue positions. The numbers to the right indicate nucleotide residue positions. Amino acids are designated by the single-letter code and * indicates the termination codon. The boxed sequences identify possible N-linked glycosylation sites. Hydrophobic regions that may identify signal and transmembrane peptides are underlined. The vertical arrow marks the most probable position of the amino-terminus of the mature protein. (See von Heijne, Nucleic Acid Res., 14: 4683 (1986)).

The amino acid sequence of LAM-1 predicted a structure typical of a membrane glycoprotein. Two potential translation initiation sites were found at nucleotide positions 53 and 92. The second initiation site conformed best to the consensus sequence for optimal initiation (A/G)CCAUG (Kozak, Cell: 44" 283–292 (1986)) and was followed by a hydrophobic region of 27 amino acids that may represent a signal peptide. The algorithm of von Heijne predicted that the most probable amino-terminus of the mature protein would be the Trp at amino acid position 52.

The LAM-1 sequence contained a second hydrophobic region between amino acids 346–368 which may be a transmembrane region. The deduced nature LAM-1 protein would have an extracellular region of about 294 amino acids containing 7 potential N-linked carbohydrate attachment sites. LAM-1 would have a cytoplasmic tail of 17 amino acids containing 8 basic and 1 acidic residues. The two cytoplasmic Ser residues may serve as substrates for phosphorylation since protein kinase C phosphorylates Ser residues that are on the carboxyl-terminal side of several basic residues. These results suggest that the processed LAM-1 protein can be isolated by conventional techniques, such as affinity column chromatography with antibody or ligand, from cell lines that normally express this receptor or from transfected cell lines. Or the protein can be synthesized by in vitro translation of the LAM-1 cDNA.

Figure 2:
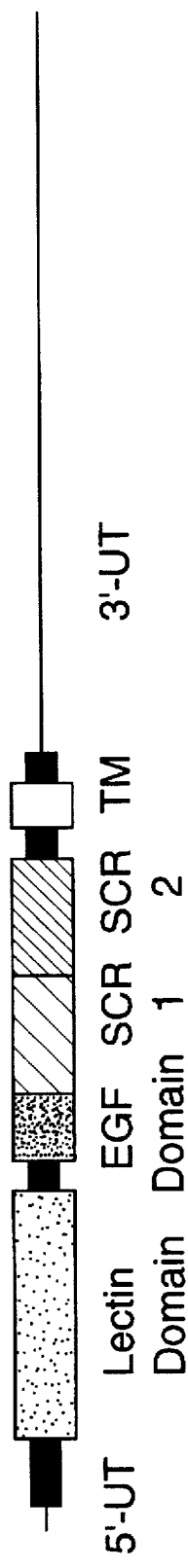
Figure 4A:
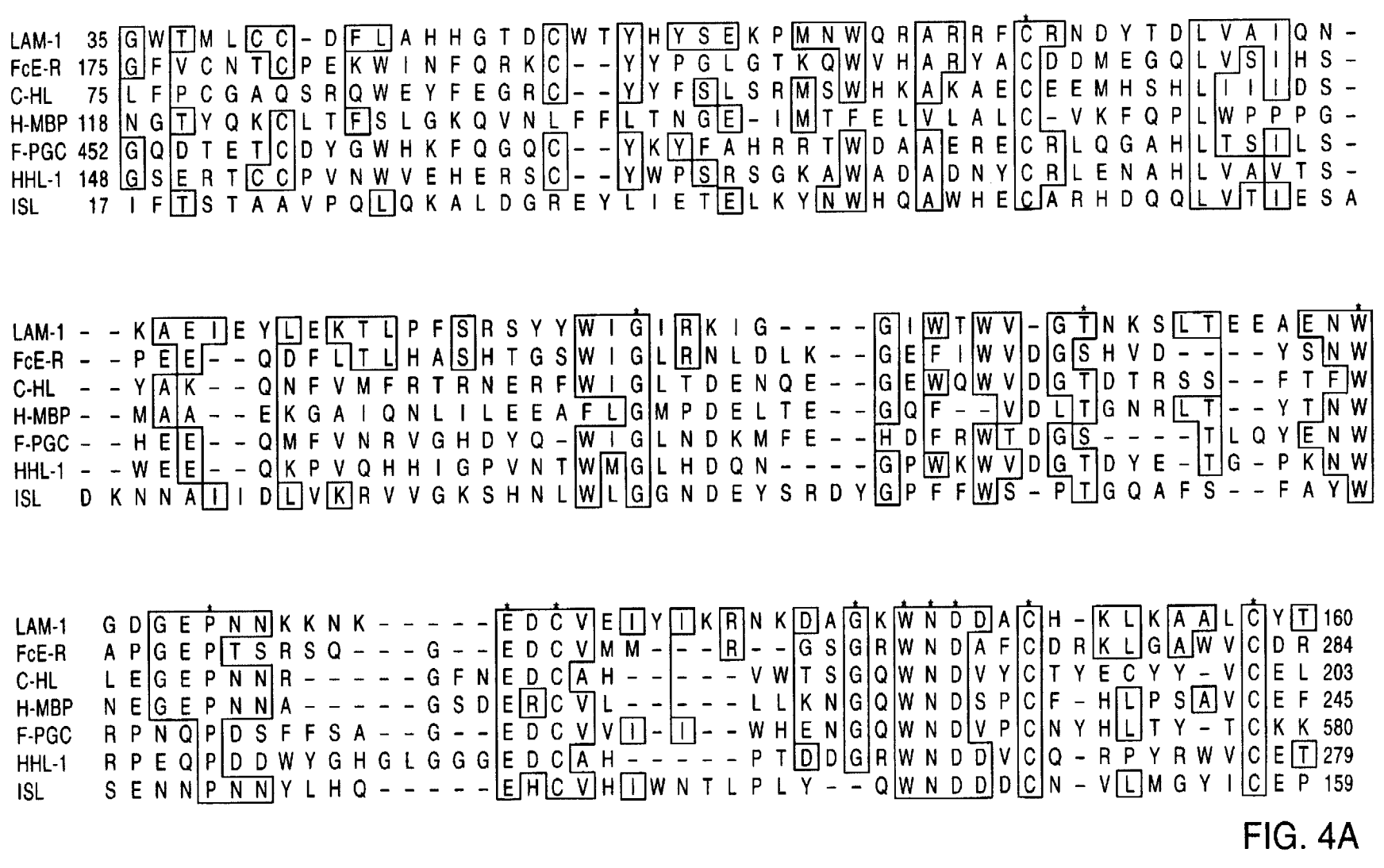

LAM-1 combines previously unrelated domains found in three distinct families of molecules: animal lectins, growth factors, and C3/C4 binding proteins. The proposed extracellular region of LAM-1 contained a high number of Cys residues (7%) with a general structure as diagrammed in FIG. 2. As indicated in FIG. 4, segments of homologous proteins are shown with the amino acid residue numbers at each end. Homologous acids are shown in boxes. Gaps have been inserted in the sequences to maximize homologies. The first 157 amino acids of the protein (FIG. 4) were homologous with the low-affinity receptor for IgE (Kikutani et al. Cell 47: 657 (1986)), the asialoglycoprotein receptor (Spiess et al., Proc. Natl. Acad. Sci. USA 82: 6465 (1985)) and several other carbohydrate-binding proteins (Drickamer et al., J. Exp. Med. 167: 1034 (1988); Krusius et al., J. Biol. Chem. 262: 13120–12125 (1987); and Takahashi et al., J. Biol. Chem. 260: 12228 (1985)). The amino acids conserved among all animal-lectin carbohydrate recognition domains are indicated (*). Although the sequence homologies were less than 30%, all the invariant residues found in animal lectin carbohydrate-recognition domains were conserved (Drickamer, J. Biol. Chem. 263: 9557 (1988)).

The next domain of 36 amino acids (FIG. 4B) was homologous (36–39%) with epidermal growth factor (EGF) (Gregory, Nature 257: 325 (1975)) and the EGF-like repeat units found in Factor IX (Yoshitake et al. Biochem. 25: 3736 (1985)) and fibroblast proteoglycan core protein (Krusius et al., supra).

Figure 4C:
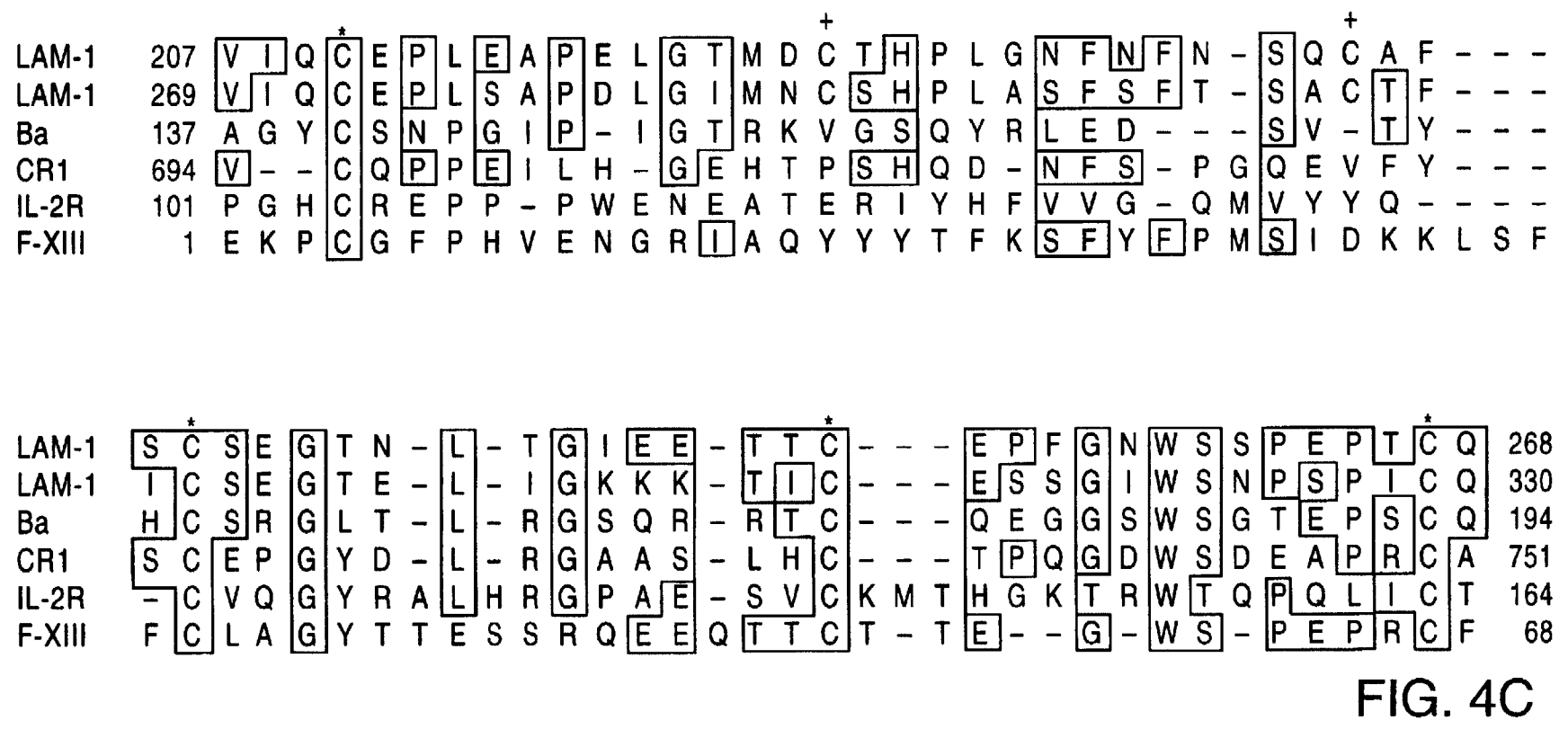

Immediately following these domains were two tandem domains of 62 amino acids each (FIG. 4C) that were homologous with the short consensus repeat units (SCR) that comprise the IL-2 receptor (Leonard et al., Nature 311: 626 (1984)), Factor XIII (Ichinose et al., Biochem. 25: 4633 (1986)) and many C3/C4 binding proteins (Klickstein et al., J. Exp. Med. 165: 1095 (1987), and Morley et al., EMBO J. 3: 153 (1984)). In contrast with all of the previously described SCR than contain four conserved Cys residues, these two SCR possessed six Cys residues. The four conserved Cys residues found in all SCR are indicated in FIG. 4C by (*); the additional conserved Cys found in LAM-1 are indicated by (+). Of the multiple SCR present in each of these proteins, the SCR with the highest homology to LAM-1 is diagrammed. A 15 amino acid spacer preceded the putative transmembrane domain.

The deduced amino acid sequence of LAM-1 is homologous with that of ELAM-1 and GMP-140. Thus, these two proteins and LAM-1 define a new family of homologous structures that are expressed by different cell lineages and that can function as receptors in cellular interactions.

Figure 5:
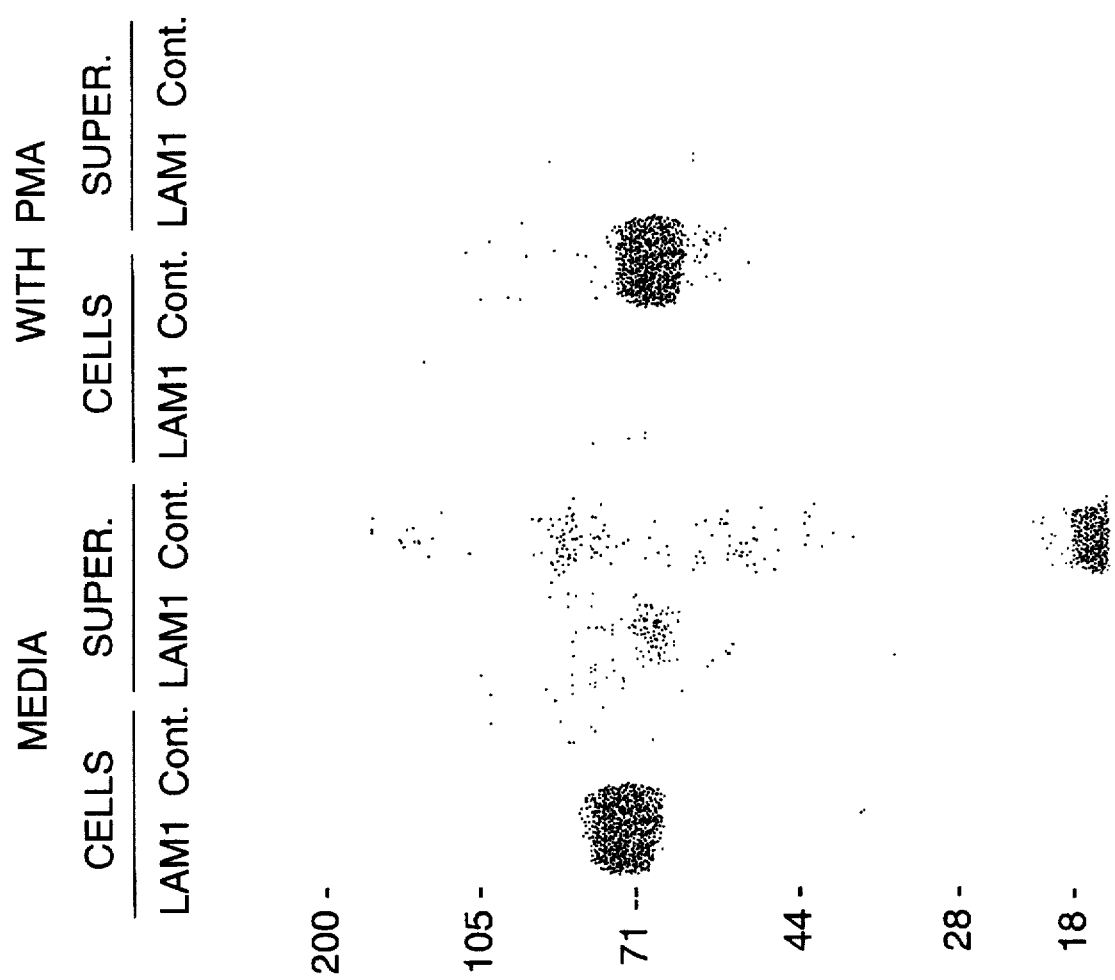
FIG. 5 depicts the immunoprecipitation of LAM-1 shed from a cell surface with anti-LAM1 antibodies or a control immunoprecipitation with an unreactive isotype-matched antibody with subsequent sodium dodecyl sulfate-polyacrylamide gel electrophoresis.

LAM-1 expression was examined on normal and neoplastic leukocytes to further understand the mechanisms that regulate leukocyte migration. The immunoprecipitation of a large fragment of LAM-1 of molecular weight 69,000 from the supernatant liquid of normal lymphocytes cultured with PMA demonstrated that LAM-1 can rapidly be cleaved from the cell surface (FIG. 5). That the LAM-1 expression is down-modulated by shedding rather than by internalization suggests that a PMA-sensitive regulatory pathway which is distinct from that which regulates down-modulation of most other surface molecules, controls the expression of LAM-1. This regulatory pathway may specifically involve the activation of PKC (Table 3). The presence of the soluble isoform of LAM-1 in the supernatant fluid of lymphocytes cultured without stimulation (FIG. 5) suggests that LAM-1 may also be continuously shed at a slow rate with its expression kept constant by the continuous synthesis of new receptors. Although the mechanism of shedding is unknown, enzymatic cleavage of the cell-surface receptor may result from the specific activation of a membrane bound protease. This is a likely method since a soluble protease secreted by activated leukocytes was not detected in this work. Alternatively, activation-induced changes in the conformation of the LAM-1 protein may expose nascent sites on LAM-1 that are then susceptible to cleavage by soluble proteases. Nonetheless, the finding that cell lines transfected with LAM-1 cDNAs rapidly modulate LAM-1 expression after PMA exposure (FIG. 14–19) suggests that the protease which cleaves LAM-1 is ubiquitous in distribution. The down-modulation of LAM-1 by shedding is similar to that of mLHR [33–34]. This is consistent with prior observations that the cell surface expression of LAM-1 is rapidly down-regulated upon activation [5,6,11]. LAM-1 removal from the cell surface may thus be necessary for the detachment of leukocytes from the endothelium so as to allow for their subsequent migration into tissues.

Figure 6:
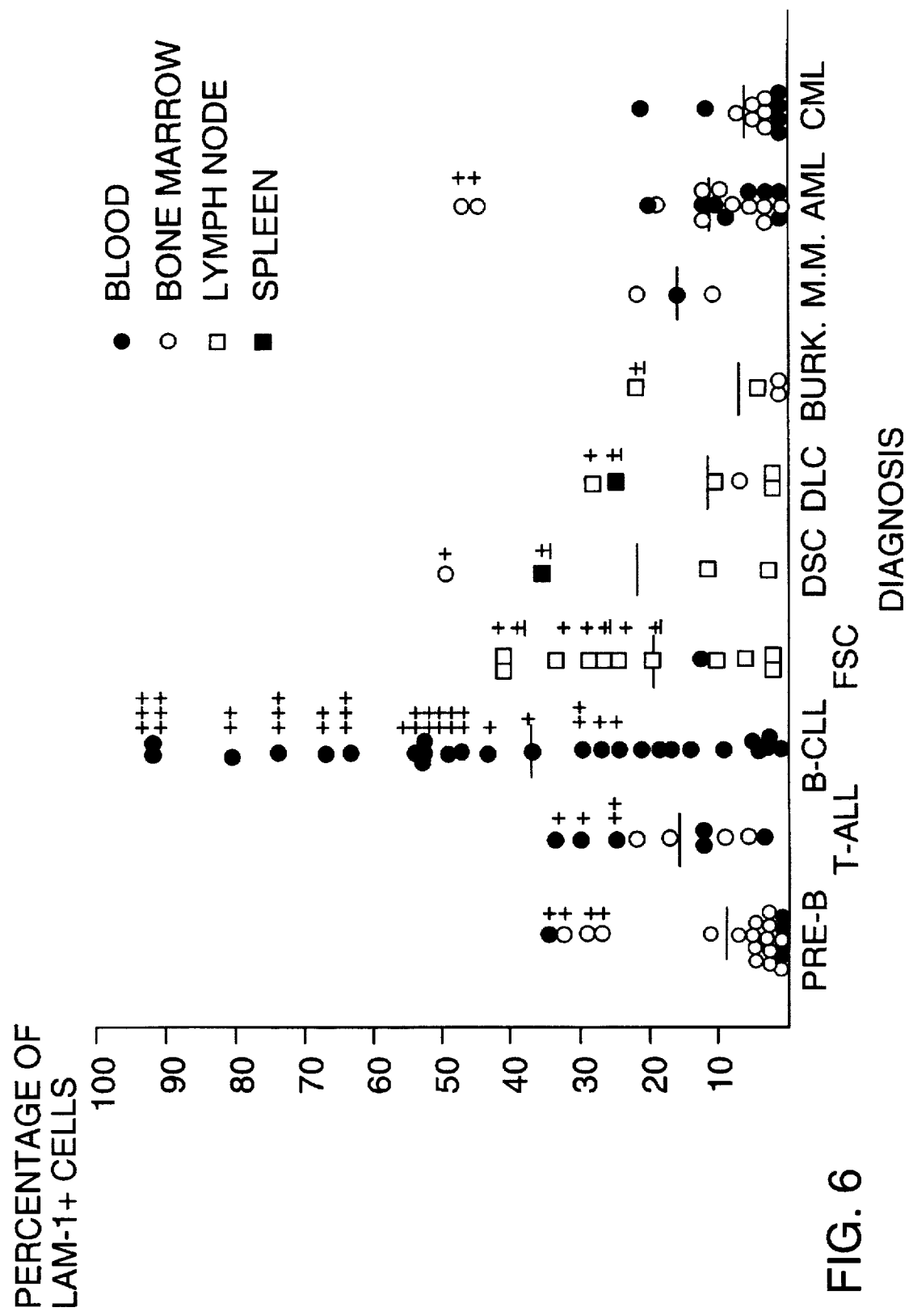
FIG. 6 depicts the percentage and reactivity of malignant cells being LAM-1 positive from patients having various forms of hematopoietic malignancies.
Figure 7:
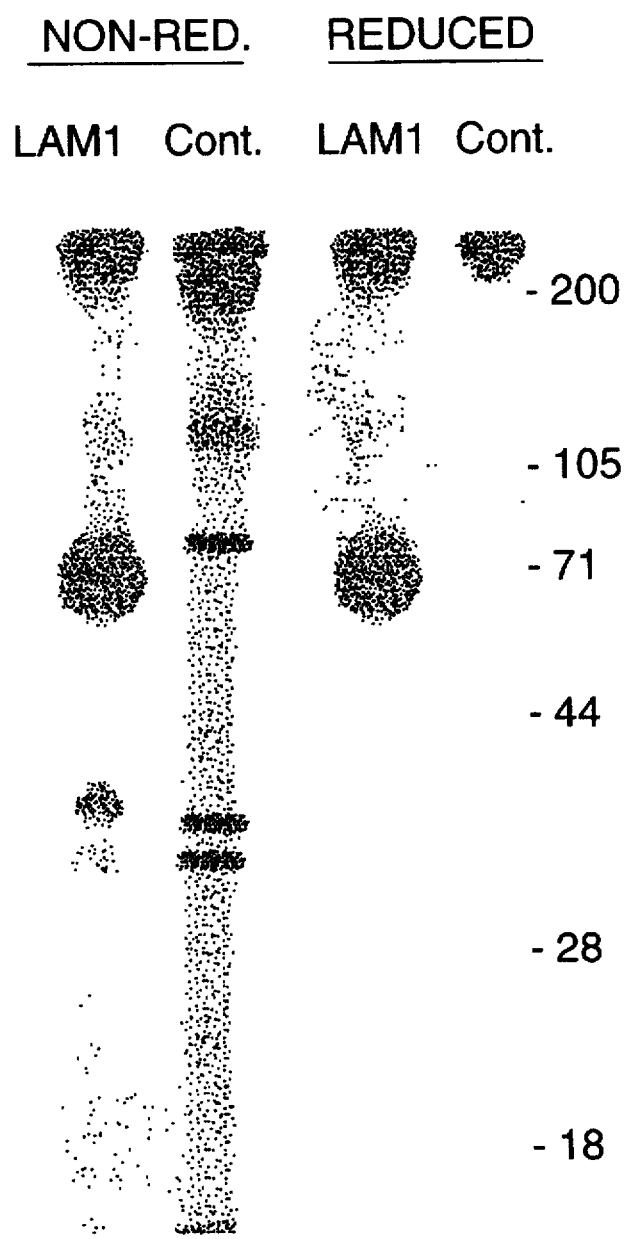
FIG. 7 depicts the immunoprecipitation of LAM-1 from the surface of iodinated CLL cells using anti LAM1-1 antibodies or an unreactive isotype-matched control with subsequent sodium dodecyl sulfate-polyacrylamide gel electrophoresis under reduced and non-reduced conditions.

LAM-1 was most frequently expressed by CLL cells among the various hematologic malignancies studied (Table 1, FIG. 6). These results extend previous studies of LAM-1 expression to TQ1 and Leu-8 using CLL and NHL cells [35–37]. Since the expression of LAM-1 was somewhat restricted among hematologic malignancies, the expression, or absence of expression, may have a major impact on the trafficking of leukemic cells and the dissemination of UHL. Immunoprecipitation of LAM-1 from CLL cells showed that it resembled the Mr 74,000 isoform of the glycoprotein expressed by normal lymphocytes (FIG. 7). In addition, LAM-1 expressed by malignant cells was functional since LAM-1 on normal lymphocytes and CLL cells were both able to bind HEV and PPME (Table 2, FIGS. 8–13). Both HEV and PPME binding was mediated by LAM-1 since the new monoclonal antibody, anti-LAM1-3, was able to completely block all HEV and PPME binding.

TABLE 1

LAM-1 Shedding Is Blocked By Protein Kinase Inhibitors

| | Without PMA* Treatment | | With PMA Treatment | |
|---|---|---|---|---|
| Cells with | % Positive | MCF No. | % Positive | MCF No. |
| Medium | 60 | 115 | 13 | 47 |
| Stauro 1 mM porine | 57 | 91 | 54 | 95 |
| 500 μM | 72 | 95 | 49 | 91 |
| 100 μM | 51 | 88 | 51 | 92 |
| 50 μM | 47 | 92 | 58 | 100 |
| H-7 1 μM | 52 | 94 | 53 | 92 |
| 500 mM | 67 | 102 | 32 | 80 |
| 100 μM | 58 | 109 | 23 | 91 |

TABLE 1-continued

LAM-1 Shedding Is Blocked By Protein Kinase Inhibitors

| Cells with | Without PMA[a] Treatment | | With PMA Treatment | |
|---|---|---|---|---|
| | % Positive | MCF No. | % Positive | MCF No. |
| 50 µM | 61 | 106 | 11 | 61 |
| NaN$_3$ 1 µM | 59 | 113 | 20 | 50 |

[a]= The percentage of cells reactive with the anti-LAM1-1 monoclonal antibody was determined by indirect immunofluorescence analysis. The relative intensity of staining of the positive cells is indicated based on the mean channel fluorescence number (MCF No.) obtained with FACS analysis (256 channels, on a 3-decade log scale. Cells treated with an unreactive monoclonal antibody had 3% positive cells with a MFC no. of 40.

TABLE 2

Binding Of Normal And Malignant Cells To HEV.

| Test | LAM-1 Expression[a] | | CD44 Expression | | Cells Bound per HEV |
|---|---|---|---|---|---|
| | % Pos. | Intensity | % Pos. | Intensity | |
| 1 | 70 | +++ | 93 | ++++ | 2.12 ± 0.05 |
| 2 | 59 | ++ | 99 | ++++ | 1.02 ± 0.22 |
| 4 | 52 | ++ | 96 | ++++ | 1.02 ± 0.32 |
| 3 | 2 | − | 65 | ++++ | 0.18 ± 0.11 |
| Normal PBL | 85 | +++ | 100 | ++++ | 4.64  0.67 |

[a]= The percentage of cells with the anti-LAM1-1 and515 monoclonal antibodies were determined by indirect immunofluorescence analysis. The relative intensity of staining of the positive cells is indicated based on a (−) being no reactivity and indicating the highest reactivity.
[b]= Values represent the mean number of cells (± SD) bound to each HEV. A total of 150 HEV were examined in each sample. The difference between the number of cells bound per HEV in LAM-1+ cases (1,2 and 4) and the LAM-1+ case (3) was statistically significant (P < 0.005) using Student's t-test statistic.

TABLE 4

PPM and HEV binding are enhanced by lymphocyte activation[1]

| Stimulus | Binding of [$^{125}$I] PPME (c.p.m. ± s.d.) | | | Cells Bound/HEV[2] (± s.d.) | |
|---|---|---|---|---|---|
| | Medium | anti-LAM1-3 | EDTA | Medium | anti-LAM1-3 |
| Medium | 4847 ± 372 | 1160 ± 104 | 578 | 1.4 ± 0.2 | 0.2 ± 0.2 |
| anti-LAM1-10 | 6868 ± 571 | 2103905± | 2030 | 1.5 ± 0.8 | 0.2 ± 0.2 |
| anti-CD2 | 17886 ± 491 | 2863 ± 689 | 965 | 2.4 ± 0.9[4] | 0.2 ± 0.2 |
| anti-CD3 | 19718 ± 1294 | 1211 ± 618 | 303 | 2.7 ± 1.0[3] | 0.2 ± 0.2 |

[1]. Blood lymphocytes were isolated, incubated for 20 minutes at 4° C. with the indicated antibodies, and anti-CD3 was crosslinked as shown by Spertini et al., Nature 349: 691–694 (1991) [See Spertini et al., Fig. 1]. After one wash, the cells were incubated with 125 I-labelled PPME (90.36 µg/ml, 2.2 × 10$^5$ c.p.m. per sample) at 40° C. for 30 minutes. Anti-LAM1-3 was added 1 minute before the addition of the test antibody and during all incubations. The calcium-independent binding of [$^{125}$I] PPME was assessed in the presence of 5 mM EDTA. Cells were washed, resuspended in PBS-BSA and layered on a 750-µl cushion of 75% (v/v) calf serum. The cell pellet was isolated and bound [$^{125}$I] PPME assessed by γ (gamma) counting. These data are representative of those obtained in three experiments. Fluoroscein-labelled PPME was iodinated by standard methods, the specific activity (2 × 10$^4$ c.p.m./ng) determined by self-displacement curve analysis, and the maximum binding capacity was 20%.
[2]. HEV binding was assessed using 12-pm freshly cut, frozen rat lymph node sections. The number of lymphocytes bound to HEV was counted on coded slides. Values are means ± standard deviation (s.d.) of four experiments, and the differences between control antibody-treated cells and anti-CD2 and anti-CD3 treated cells were significant.
[3]. P < 0.05 using the paired Student's t-test.
[4]. P < 0.01 using the paired Student's t-test The level of HEV binding was also proportional to the quantity of LAM-1 expressed, and LAM-1 negative cells were unable to bind HEV and PPME. LAM-1 was also shed from the surface of CLL cells following PMA exposure

TABLE 3

EXPRESSION OF ADHESION MOLECULES BY MALIGNANT LEUKOCYTES

No. of cases expressing antigen/number examined[a] (mean % among positive cases)

| Diagnosis | LAM-1 | CD44 | CD11a | CD11b | CD18 | CD54 | CD 58 |
|---|---|---|---|---|---|---|---|
| Pre-B-ALL | | | | | | | |
| CD10+ | 4/15 (32) | 10/12 (67) | 1/8 (46) | 0/15 | 1/12 (40) | 4/13 (33) | 6/13 (69) |
| 5 CD10− | 0/6 | 5/5 (80) | 0/6 | 0/5 | 0/5 | 0/5 | 2/5 (55) |
| T-ALL | 2/10 (31) | 8/9 (67) | 3/8 (59) | 0/2 | 5/10 (49) | 4/10 (46) | 1/10 (6.2) |
| B-CLL | 16/27 (55) | 16/18 (76) | 3/14 (45) | 0/21 | 3/18 (32) | 1/18 (31) | 1/18 (43) |
| B-lymphoma | | | | | | | |
| FSC | 6/12 (32) | 9/11 (59) | 8/9 (56) | 0/12 | 9/11 (38) | 5/11 (50) | 2/11 (49) |
| 10 DCS | 2/4 (41) | 4/4 (70) | 1/4 (90) | 0/3 | 1/4 (90) | 3/4 (40) | 1/4 (77) |
| DLC | 1/6 (27) | 6/6 (59) | 5/6 (55) | 0/6 | 4/4 (49) | 3/6 (54) | 2/6 (53) |
| Burkitt's | 0/4 | 2/4 (52) | 0/4 | 0/4 | 0/4 | 1/4 (72) | 0/4 |
| M. Myeloma | 0/3 | 2/2 (84) | 3/3 (53) | 2/2 | 0/3 | 1/3 (52) | |
| AML | 2/19 (44) | 16/16 (79) | 6/11 (50) | 5/19 (42) | 11/16 (41) | 1/16 (47) | 9/16 (61) |

Figure 8:
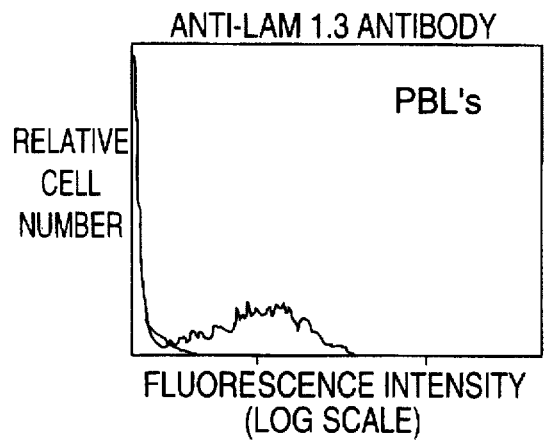
FIGS. 8–13 depict indirect immunofluorescence results obtained with the anti-LAM1-3 antibody and PPME-FITC.
Figure 9:
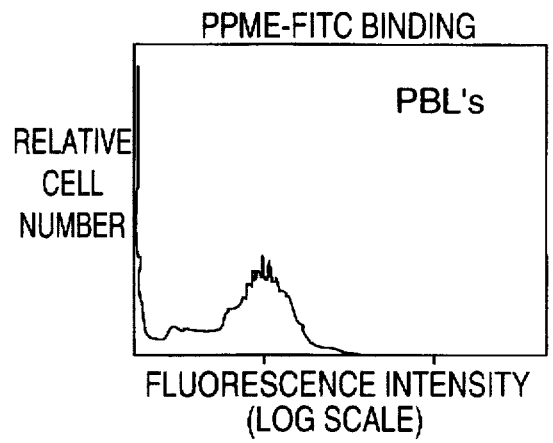
Figure 10:
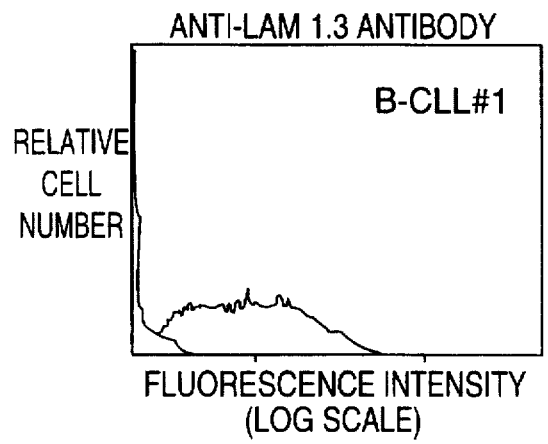
Figure 11:
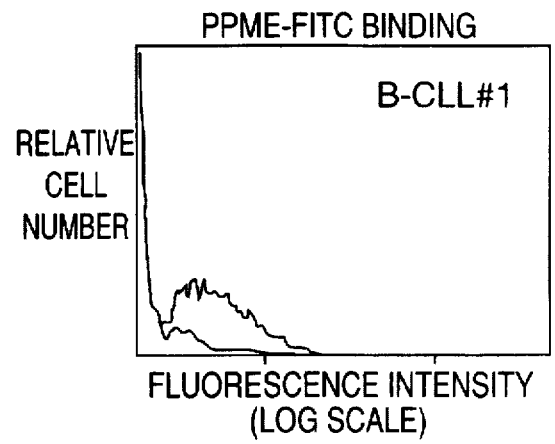
Figure 12:
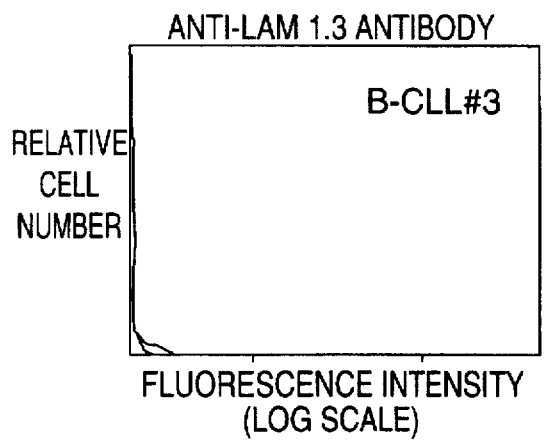
Figure 13:
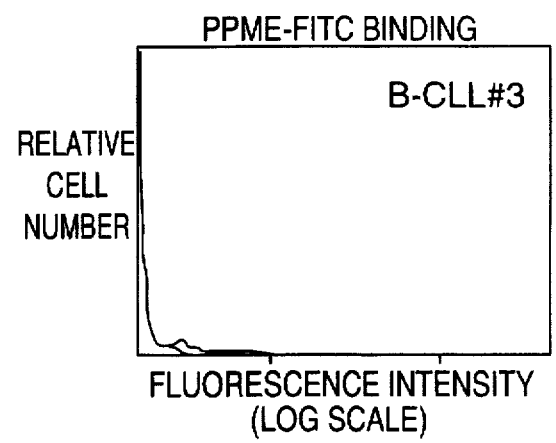
Figure 14:
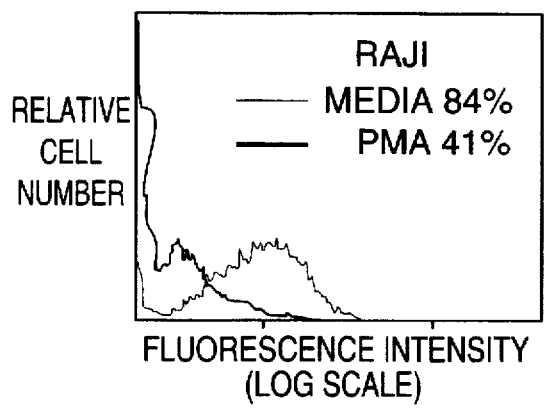
FIG. 14–19 depicts the modulation of cell surface LAM-1 by malignant cells and cDNA transfected cells after PMA exposure.
Figure 15:
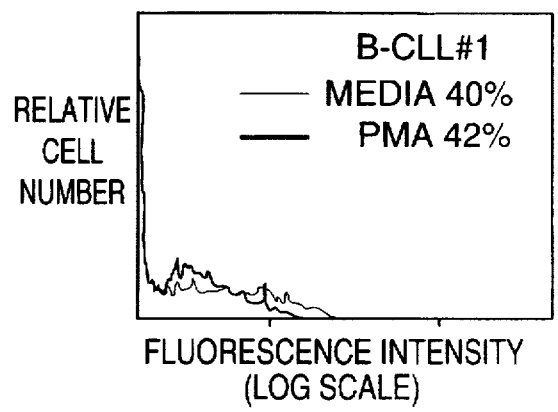
Figure 16:
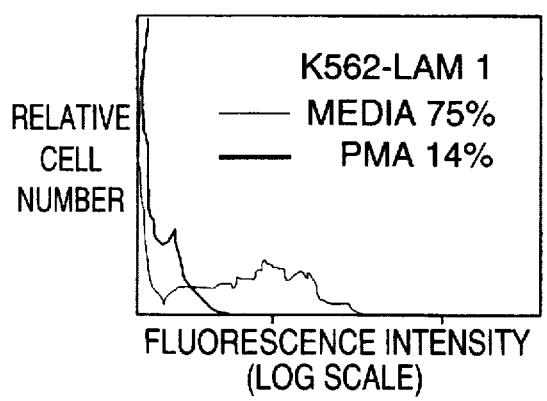
Figure 17:
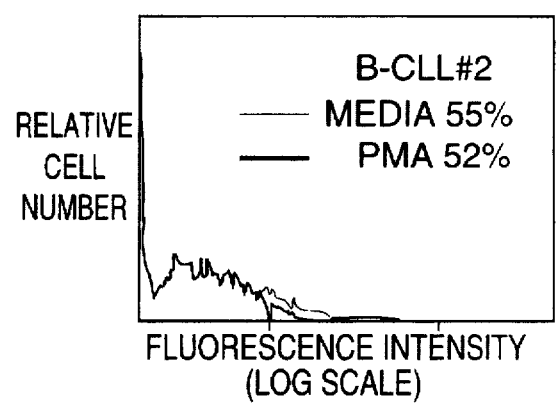
Figure 18:
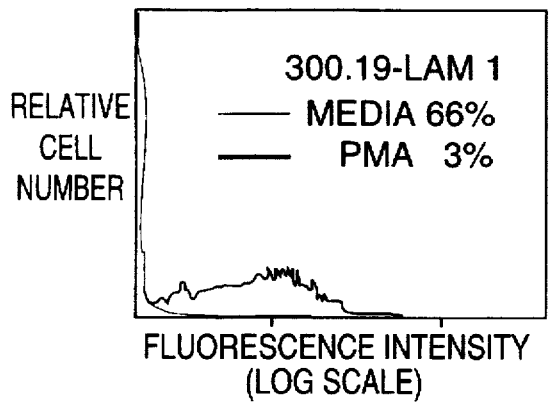
Figure 19:
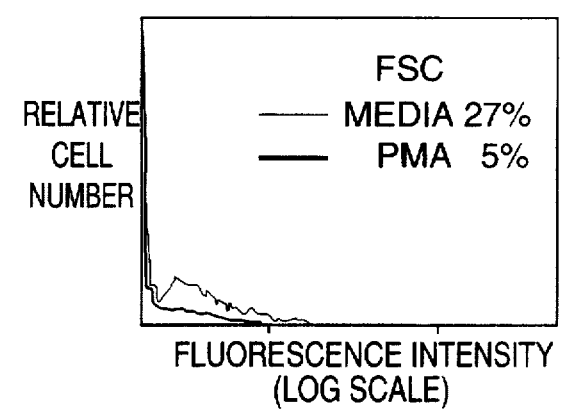

(FIG. 8). However, the signalling pathway for shedding may be less active in some CLL cells since the time-course of LAM-1 shedding was slower than in normal lymphocytes. Malignant cells, therefore, express functional LAM-1 receptors that are indistinguishable from their normal counterparts on normal cells and the expression of LAM-1 by CLL cells correlated with the high tendency of these cells to localize into peripheral LN.

In contrast to LAM-1, CD44 expression was found to be consistently expressed at high levels among the leukemias and NHL examined, while the expression of other adhesion molecules CD11/CD18, CD54 and CD58 was variable (Table 1). Expression of CD44 did not correlate with the ability of cells to bind to HEV since LAM-1 negative CLL cells that expressed high levels of CD44 did not bind to HEV in frozen section assays (Table 2) similar to what was shown by one research group using lymphoblastoid cell lines [17]. CD44 constitutes a broadly distributed family of glycoproteins expressed on virtually all hematopoietic cells, fibroblasts, epidermal, glial and melanocytic origin cells [21,38]. Although CD44 was initially regarded as the human homing receptor equivalent of the mLHR [28,29], it may be more generally involved in cell-cell or cell-matrix binding as a receptor for hyaluronate [39]. Previous studies have also suggested that CD44 is involved in the dissemination of NHL [40]. During the work resulting in the present invention, however, no clear relationship could be inferred from the results of CD44 expression alone.

LAM-1 is expressed on most neutrophils, monocytes, normal myeloid progenitor cells and early erythroid precursors in BM (bone marrow) [6]. The co-expression of this homing receptor and other adhesion molecules may control the physiological retention (homing) of these cells in BM. The homing of intravenously transplanted hematopoietic stem cells is mediated by a recognition system with galactosyl and mannosyl specificities [41] which might also mimic the LAM-1 ligand [42]. In this regard, it is noted that AML and CML cells were found to lack expression of LAM-1. Unlike the situation with lymphoid tumors, this is in sharp distinction with the high level expression of LAM-1 on normal myeloid cells. The absence of LAM-1 expression on most AML and CML cells might favor the passage of these cells into the bloodstream. Although overnight culture of CML cells did not result in the expression of LAM-1 on the cell surface, the overall lack of LAM-1 expression by these cells indicates that further investigations of the regulation of LAM-1 by leukemic myeloid cells is warranted.

There is growing evidence in mouse and man that the binding of lymphocytes to HEV of peripheral LN and the migration of normal leukocytes from blood into inflammatory lesions is controlled by several adhesion molecules whose expression is coordinately regulated [5,6,33,43]. It is likely that similar mechanisms will contribute to the spread of leukemias and lymphomas. In one murine study, the expression of functional receptors for HEV was shown to control the hematogenous dissemination of malignant lymphocyte populations to HEV bearing organs [16]. Lymphomas that bound well to HEV disseminated weakly vias the blood, ultimately involving all LN groups symmetrically. In contrast, gross involvement of LN by non-binding lymphomas was limited to nodes draining localized tumors which formed at the site of injection. These results suggested that the expression of functional receptors for HEV either controls the hematogenous dissemination of malignant lymphocyte populations to HEV-bearing organs, or is co-regulated with factors that determine metastatic behavior [16]. In humans, the expression of functional HEV binding molecules such as LAM-1, on CLL and low-grade lymphoma cells may also contribute to the wide-spread dissemination of these malignant cells to LN as occurs with normal lymphocytes.

Materials and methods

Cell Samples

Peripheral blood mononuclear cells (PBMC) were isolated by Ficoll-Hypaque density gradient centrifugation of blood, bone marrow (BM) samples and single cell suspensions of LN. Cells were obtained by protocols approved by the Human Protection Committee of the Dana-Farber Cancer Institute. Tumor type was classified according to conventional morphological, cytological and immunophenotype criteria. Tumor cell lineage was determined by analysis of antigens (Ag) including surface and cytoplasmic immunoglobulin (Ig), HLA-DR Ag, CD1, CD2, CD3, CD4, CD5, CD6, CD8, CD9, CD10, CD11b, CD13, CD14, CD19, CD20 and CD33. Cells were examined immediately after isolation or were immediately cryopreserved and kept frozen in liquid nitrogen until used. The frequency of malignant cells was always greater than 90% in every sample examined.

Antibodies

The anti-LAM-1 monoclonal antibodies anti-LAM1-1 and anti-LAM1-2 and the monoclonal antibody anti-TQ1 have been previously described [5,8]. The anti-LAM1-3 antibody (IgG1) of the claimed invention was generated by the fusion of NS-1 myeloma cells with spleen cells from BALB/c mice that were repeatedly immunized with cells of the mouse pre-B cell line 300.19 transfected with a LAM-1 cDNA as described [5]. The antibodies used in these studies included: 2F12 (CD11a) and 10F12 (CD18) [18] which were gifts from J. Ritz (Dana-Farber Cancer Inst., Boston, Mass.); TS2/9 (CD58, antiLFA-3) [19] and RR 1/1 (CD54, anti-ICAM-1) [20] which were gifts from T. A. Springer (Center for Blood Research, Boston, Mass.); 515 (CD44) [21] a gift from G. S. Kansas (Dana-Farber Cancer Inst.); and 904 (CD11b) [22].

Immunofluorescence analysis

Indirect immunofluorescence analysis was performed on viable cells isolated by Ficoll-Hypaque density gradient centrifugation. The expression of LAM-1, CD11a, CD1b, the β subunit of CD11 complex (CD18), CD44, CD54, and CD58 was examined by indirect immunofluorescence with flow cytometry analysis (Coulter Epics C, Coulter Electronics, Hialeah, Fla.). Isotype-matched murine antibodies that were unreactive with human leukocytes were used as negative controls. Cells were incubated with each monoclonal antibody for 20 minutes on ice, washed, and treated with FITC-conjugated goat anti-mouse Ig reagents (Southern Biotechnology Associates, Birmingham, Ala.).

The ability of normal lymphocytes and B-CLL cells to bind the fluorescein derivative of PPME (fl-PPME) (a gift of S. D. Rosen, University of California, San Francisco, Calif.) was assessed by incubating cells for 30 minutes on ice with 100 µl ml of fl-PPME at 30 µg/ml in phosphate buffered saline (PBS). After washing twice, the binding of fl-PPME was examined by flow cytometry analysis as described [23, 24]. HEV binding assay.

The in vitro HEV binding assay was performed using frozen tissue sections of human or rat peripheral LN using the methods of Stamper and Woodruff [25] and Butcher, et al. [26] as described [5]. Blocking of cell binding using the anti-LAM-1 monoclonal antibodies was carried out using freshly cut-frozen rat lymph node sections and the antibodies were used as ascites fluid at dilutions of 1:100.

13

Immunoprecipitation analysis

Cells were washed twice, resuspended in RPMI 1640 medium (Sigma, St. Louis, Mo.) at a concentration of $30 \times 10^6$ cells/ml) and treated for 40 minutes at room temperature with neuraminidase (0.1 U/mi, Calbiochem, La Jolla, Calif.) and then labelled by lactoperoxidase-catalyzed iodination. After washing, the cells were lysed in buffer containing It (v/v) NP-40 as described [27]. Cell lysates were precleared for 2 hours using 3 µl ml of murine ascites fluid (isotype matched antibody) and 25 µl of a 50% (v/v) suspension of Gammabind-G Agarose (Genex, Gaithersburg, Md.). Cell lysates were precleared again overnight. Half of the precleared lysate was then incubated with 3 µl of anti-TQl ascites fluid, 3 µl of anti-LAMl-1 ascites fluid, and 50 µl of Gammabind-G with constant rotation at 40C for 18 hours. The other half of the lysate was treated similarly using 3 µl ml of isotype-matched murine ascites fluid. Immunoprecipitates were washed and analyzed by SDS-PAGE. Molecular weights (Mr) were determined using standard molecular weight markers (BRL, Bethesda, Md.).

In experiments designed to study LAM-1 shedding, LAM-1 was immunoprecipitated as described above from the supernatant fluid and the pellet of PBMC that had been cultured for 60 minutes at 37° C. in RPMI 1640 medium alone or in RPMI medium containing PMA (100 ng/ml, Sigma, St. Louis, Mo.). In addition, expression of LAM-1 was assessed after incubation of the calls with PMA (10 nM for 30 minutes) following the prior culture of the cells with sodium azide (Sigma) or the protein kinase inhibitors, 1-(5-Isoquinolinyl-sulfonyl)-2-methylpiperazine (H-7, Calbiochem) and staurosporine (Sigma) for 30 minutes at 37° C.

Discussion of FIGS. 5–19

FIG. 5

LAM-1 is shed from the cell surface into the culture medium. PBMC were surface iodinated and cultured for 60 minutes in medium or medium containing 100 ng/ml PMA. The supernatant fluid and cells were harvested and immunoprecipitated with anti-LAM-1 antibodies or an unreactive isotype matched control antibody (Cont.). Immunoprecipitated materials were electrophoresed on a 7.5%. SDS acrylamide gel under reducing conditions followed by autoradiography. The migration of known molecular weight standards are shown in kilo-Daltons (kDa).

FIG. 6

The frequency of LAM-1 expression by malignant cells. Calls from 118 patients with various forms of hematopoietic malignancies were examined for surface LAM-1 expression using the anti-LAMl-1 monoclonal antibody in indirect immunofluorescence assays with flow cytometry analysis. In each instance, the background staining for each sample was determined using an unreactive isotype-matched monoclonal antibody and the level of background staining (usually less than 5%) was subtracted from the values shown. The horizontal bars represent the mean frequency of reactive cells. [Abbreviations: Pre-B, pre-B acute lymphoblastic leukemia; T-ALL, T cell acute lymphoblastic leukemia; B-CLL, B type chronic lymphocytic leukemia; FSC, follicular small cleaved cell lymphoma; DSC, diffuse small cleaved cell lymphoma; DLC, diffuse large cell lymphoma; Burk., Burkitt's type lymphoma; M.M., multiple myeloma; AML, acute myslogenous leukemia; CML, chronic myelogenous leukemia]. The relative fluorescence staining intensity of the malignant cells is indicated where the positive population could be identified as a distinguishable peak from background fluorescence staining: ±where a shoulder of positively stained cells was evident, +, where a separate peak of positive cells was identified with weak fluorescence; ++, a definite separate peak of fluorescence positive cells of moderate fluorescence; +++, a peak of fluorescence positive cells of the same intensity as normal blood lymphocytes. The tissue source of all malignant cells is also indicated.

FIG. 7

Analysis of LAM-1 immunoprecipitated from B-CLL cells. Detergent lysates of surface iodinated cells ($45 \times 10^6$) were immunoprecipitated with the anti-TQl and anti—LAMl-1 antibodies (LAM-1) or an unreactive isotype-matched antibody control (Cont.). Immunoprecipitated materials were divided and analyzed under non-reducing and reducing conditions on a 12% SDS polyacrylamide gel followed by autoradiography. Molecular weights (kDa) were determined by the migration of known protein standards.

FIGS. 8–13

Normal human lymphocytes and CLL cells are capable of binding PPME through LAM-1. Cells were examined for LAM-1 expression by indirect immunofluorescence analysis after treatment with the anti-LAMl-3 monoclonal antibody (dark line) or with an unreactive isotype matched antibody (thin line). Cells were also reacted with FITC-conjugated PPME after treatment with the anti-LAMl-3 antibody (thin line) or an unreactive control antibody (dark line). The fluorescence intensity of cell staining was analyzed by flow cytometry.

FIGS. 14–19

Modulation of cell surface LAM-1 by malignant cells and cDNA transfected cells after PMA exposure. Cells transfected with LAM-1 cDNA, K562-LAMl and 300.19-LAMl, and malignant cells that expressed LAM-1 were either cultured for 90 minutes in media or in media containing 10 ng/ml PMA. Following culture, the cells were examined for LAM-1 expression using the anti-LAMl-1 antibody in indirect immuno-fluorescence assays with flow cytometry analysis. Cells were also stained with an unreactive control antibody and the level of background staining was always less than 5%. The frequency of cells expressing LAM-1 is shown with the number of background staining cells subtracted.

Results

LAM-1 is released from the cell surface following PMA exposure

Immunoprecipitation experiments were carried out to determine the fate of LAM-1 after modulation from the surface of PBMC exposed to PMA [5]. Surface iodinated cells were cultured for 60 minutes in RPMI medium alone or medium containing PMA. After culture, the supernatant fluid and cells were separated, and the cells were lysed with detergent. The cell lysate and supernatant fluid were immuno-precipitated with a combination of anti-LAMl-1 and anti-TQl antibodies that bind to different epitopes of LAM-1 [51, and together are more efficient for immunoprecipitation. The cells were also treated with neuraminidase prior to surface iodination since LAM-1 may be more readily immuno-precipitated after the removal of sialic acid residues. Treatment of cells with PMA resulted in a dramatic loss of immunoprecipitable LAM-1 from the cell surface with a concomitant increase in the level of LAM-1 precipitated from the supernatant fluid. Incubation of cells in medium without PMA also resulted in a small amount of LAM-1 being found in the supernatant fluid (FIG. 5). The molecular weight of LAM-1 precipitated from the supernatant fluid was slightly smaller (by about 5 kDa) than the species of LAM-1 found on the cell surface. Interestingly, the residual LAM-1 found on the cell surface of PMA-treated cells was most similar in molecular weight to that of the LAM-1 found in the supernatant fluid. The quantitative recovery of labeled LAM-1 from the supernatant fluid, in comparison to the amount immunoprecipitated from solubilized cells, demonstrates that a major portion of LAM-1 is shed from the cell surface and not internalized following PMA exposure.

Expression of adhesion molecules by malignant leukocytes

The expression of LAM-1 and other cell surface molecules known to be involved in lymphocyte adhesion and migration was examined on malignant leukocytes from 118 patients by indirect immunofluorescence analysis. LAM-1 expression was most frequently demonstrated on CLL cells and among lymphomas classified as follicular (FSC) and diffuse small cleaved cell lymphoma (DSC) (Table 3). On the other hand, most acute myeloblastic leukemia (AML), acute lymphoblastic leukemia (ALL), chronic myelocytic leukemia (CML), diffuse large cell lymphomas (DLC), Burkitt's lymphomas and multiple myelomas were LAM-1 negative. The level of cell surface LAM-1 expression was highest on CLL cells; and in 11 of 16 cases that expressed LAM-1, more than 50% of cells were LAM-1+ (FIG. 6). In general, the fluorescence intensity level of LAM-1 staining correlated with the frequency of LAM-1+ cells such that most malignant cell populations with less than 25% positive cells failed to express LAM-1 at easily detectable levels.

CLL cells rarely expressed adhesion molecules other than LAM-1, with the exception of CD44 (Table 3), which has also been associated with lymphocyte homing [28,29]. More than 90% of the cell samples were CD44+, consistent with its ubiquitous distribution on normal hematopoietic cells. Ninety-three percent of the leukemias and 84% of the B-NHL were positive for this antigen and generally greater than 60% of the cells were CD44+. In general, the expression of CD11a, CD11b, CD18, CD54, and CD58, was more heterogeneous (Table 3).

Incubating normal blood lymphocytes for about 8–16 hours at 4° C. can result in complete loss of LAM-1 from the cell surface [30]. However, the cryopreservation of PBMC, LAM-I+ lymphoblastoid cell lines and freshly isolated LAM-1+ malignant cells did not appreciably alter the qualitative expression of LAM-1. A minor quantitative decrease in LAM-1 expression was observed that could be reversed by culturing the cells for about 8–16 hours in RPMI 1640 medium with 10% FCS (fetal calf serum). Consequently, 37 of the samples of malignant cells were re-examined following the above culture. This treatment, however, did not result in the appearance of, LAM-1 on the call surfaces or a significant increase in the frequency of LAM-1 expression in any case.

Structure of LAM-1 expressed by malignant cells

Anti-LAM-1 antibodies were used to immunoprecipitate LAM-1 from CLL cells. LAM-1 migrated with a Mr of 68,000 under non-reducing conditions and at 73,000 after reduction (FIG. 7), similar to LAM-1 immunoprecipitated from normal lymphocytes (FIG. 5). Therefore, it appears that normal and malignant lymphocytes express the same cell-surface LAM-1 protein.

LAM-1 receptor function

The relationship between LAM-1 expression and the ability of cells to bind to human peripheral LN HEV was examined using cells from normal circulating blood, three LAM-1 positive CLLs and one LAM-1 negative CLL. Cells were assessed for their ability to bind HEV of human peripheral LN using the frozen section assay of Stamper and Woodruff [25]. The LAM-1+ cells bound to HEV at levels which corresponded to the amount of LAM-1 expressed on their cell surface, while the LAM-1 CLL cells did not bind (Table 2). In contrast, CD44 expression was quite high on all of the cell samples examined and did not correlate with HEV adhesion. Additional studies examined the ability of anti-LAM-1 monoclonal antibody to block HEV binding. A new antibody, anti-LAM1-3, was able to specifically block 92 to 95% of normal lymphocyte and LAM-1+ CLL cell binding (cells from Table 2) to rat peripheral LN HEV. In contrast, the binding of a different antibody, anti-LAM1-10, reactive with a different epitope of LAM-1, had no detectable effect on HEV binding. (See Table 4). Therefore, the levels of LAM-1 expression correlated with the ability of cells to bind HEV and antibodies reactive with LAM-1 specifically blocked binding.

The ligand for the mLHR is mimicked by the mannose 6 phosphate-rich polysaccharide PPME [24]. Therefore, the ability of normal human lymphocytes and CLL cells to bind fluoresceinated PPME was examined to further characterize the functional capacity of human LAM-1. Both normal blood lymphocytes and LAM-1+ CLL cells were able to bind PPME, while LAM-1– CLL cells did not bind PPME (FIGS. 8–13). The specificity of PPME binding to LAM-1 was verified by the ability of anti-LAM1-3 antibody to completely block PPME binding to the cells (FIGS. 8–13).

Modulation of LAM-1 expression

The exposure of normal lymphocytes and neutrophils to phorbol esters induces a rapid disappearance of LAM-1 from the cell surface [5,6]. Therefore, modulation of LAM-1 expression after PMA stimulation was investigated on cells from 16 patients with CLL. After 90 minutes exposure to PMA, LAM-1 expression was completely lost in 4 cases, whereas it was only partially down-modulated in the 12 remaining cases. In 10 of these 12 cases, the down-modulation of LAM-1 expression was similar to that of RAJI calls cultured simultaneously under the same conditions (FIGS. 14–19), while it was only minimal in two cases (B-CLL #1 and #2, FIGS. 14–19). In cells from one patient with a FSC type NHL, PMA induced an almost complete modulation of LAM-1 expression after 90 minutes of stimulation (FIGS. 14–19). In six LAM-1+ CLL cell samples tested further, PMA exposure lead to the complete loss of LAM-1 expression after 180 to 360 minutes of culture with PMA with similar kinetics to those of RAJI cells treated simultaneously. These experiments were also carried out using cryo-preserved blood lymphocytes and RAJI cells as controls, with no appreciable affect on the ability of the cells to modulate LAM-1 expression after PMA exposure.

The down-modulation of LAM-1 expression was also investigated in LAM-1 cDNA transfected cells. The erythroleukemia cell line, K562, and the mouse pre-B cell line, 300.19, were transfected with LAM-1 cDNA as described (51, generating cells that express relatively high levels of cell surface LAM-1 (FIGS. 14–19). In contrast to what was observed with RAJI cells and the majority of CLL cells, 90 minutes exposure of these calls to PMA induced an almost complete loss of LAM-1 from the cell surface.

The role of PKC in LAM-1 shedding was further assessed by culturing normal blood lymphocytes with protein kinase prior to their exposure to PMA. Treatment of cells with both H-7 [31] and staurosporine [32] inhibited shedding, albeit at different optimal molar concentrations (Table 1). In contrast, pretreatment of lymphocytes with sodium azide did not inhibit down-modulation of cell surface receptor. However the shedding process required on—going metabolism since PMA treatment at 4° C. did not induce detectable LAM-1 shedding (data not shown). Thus, PKC may regulate cell Surface receptor expression through direct phosphorylation of LAM-1 which may signal for cleavage or through kinase regulation of protease activity.

Shedding of LAM-1 does not result from the activation—induced secretion of a soluble protease. Neutrophils ($10^7$/ml) were activated with lineage-specific cytokines such as granulocyte/macrophage-CSF, to induce complete LAM-1 shedding [6]. The supernatant fluid of these cultures was harvested and used as culture medium for lymphocytes or LAM-1 cDNA transfected cells for 120 minutes at 37° C. This treatment did not induce detectable LAM-1 shedding from the surface of lymphocytes as assessed by flow cytometry analysis. In addition, the activation of neutrophils by lineage-specific stimuli in the presence of lymphocytes failed to induce detectable loss of lymphocyte LAM-1 while neutrophil shedding of LAM-1 was complete. Thus, it appears that a membrane anchored protease cleaves LAM-1 from the cell surface or that cellular activation is required for cleavage to occur.

LAM-1 expression on malignant leukocytes from tissue

LAM-1 expression may be down-regulated during lymphocyte entry into tissues and this down-regulation is reversible in culture [5]. Malignant cells isolated from the highly infiltrated spleen of a CLL patient were found to express LAM-1 at a lower level than the CLL cells found in his peripheral blood (i.e. 65% on blood cells and 25% on splenocytes). The percentage of LAM-1 positive spleen cells was comparable to that of the patients peripheral B-CLL cells stimulated for 180 minutes with PMA. This suggests that LAM-1 expression was decreased with entry of the CLL cells into the spleen as occurs with normal lymphocytes.

LN cells from patients with NHL (two patients with FSC, one with DLC and two with DSC) and leukemia BM cells (from two patients with AML, one with ALL and one with CML) were incubated overnight at 37° C. In RPMI 1640 medium containing 10% FCS. Contrary to the results obtained under the same conditions with normal spleen cells [5], an increase in LAM-1 expression was not detected on the malignant cells after culture, suggesting that LAM-1 was not expressed constitutively on these cells.

Table 5, below, lists a number of the properties of the monoclonal antibodies anti-LAM1-1, -2 and -3. Lines 1, 2, and 3 give the name of the antibody, the isotype and the differences in staining intensity. These properties are not necessarily indicative of differences in epitope recognition.

Functional studies of the antibodies are given in lines 4–6. These results demonstrate that different parts of the LAM-1 molecule are recognized by the different monoclonal antibodies. Lymph nodes contain structures called high endothelial venules (HEV) which are utilized by lymphocytes to enter the lymph nodes (the site of immune responses) from the blood stream. Emigration of lymphocytes into the node has been shown to be mediated by adhesion molecules which allow the cells to stick to and then traverse the venule. This process has been studied by incubating isolated lymphocytes with lymph node tissue sections. When the sections are incubated with lymphocytes alone, the cells will adhere to HEV, and the number of adherent cells can be counted. Various monoclonal antibodies, including the LAM-1 antibodies, have been used to block this binding. Line 4 gives the results of such studies for LAM1-1, -2 and -3.

The polysaccharide PPME mimics the natural ligand for the LAM-1 molecule. Since PPME can be directly fluoresceinated, it is possible to study the effect of the various monoclonal antibodies on the interaction of LAM-1 and PPME. Line 5 details the results using cells which were first incubated with a LAM-1 monoclonal antibody, followed by treatment with PPME-FITC. Anti-TQ1, anti-LAM1-2 and anti-LAM1-3 blocked PPME binding and anti-LAM1-1 enhanced PPME binding. These results demonstrate the functional (and by extrapolation, -@he specificity) differences between the antibodies.

The results shown on line 6 were obtained by the reverse of the line 5 experiment; i.e., cells were first incubated with unlabelled PPME, followed by indirect immunofluorescence with the LAM-1 antibodies. As in line 5, differences in the effects of incubation with PPME on subsequent monoclonal antibody binding indicates that the various monoclonal antibodies recognize different epitopes of the LAM-1 molecule.

Lines 7–10 detail the results of studies in which the ability of a given monoclonal antibody to block the subsequent binding of other monoclonal antibodies was analyzed. Blocking of one antibody by another provides evidence that the two antibodies in question recognize epitopes which are identical or close together on the molecule. The results in Table 5 indicate that anti-LAM1-1 does not block anti-LAM13, indicating that their epitopes are different. Anti-LAM12, however, does block anti-LAM1-3, indicating that these epitopes are at least close to each other. There are differences between anti-LAM1-2 and anti-LAM1-3, however, because of the different response they generate regarding Leu 8. Anti-LAM1-2 does not block Leu 8, whereas andi-LAM1-3 strongly blocks it. Species cross-reactivity gives further indications of the differences which exist between the antibodies and the epitopes that they identify.

Line 11 gives the results of the domain mapping regarding the monoclonal antibodies. The LAM-1 molecule contains three domains which are:

(a) a lectin-like domain (L);

(b) an epidermal growth factor-like domain (EGF); and (c) a domain of short consensus repeats (SCR).

In order to determine which domain was recognized by each antibody, cDNAs were constructed which contained the information coding for:

(1) the whole LAM-1 molecule;

(2) the L, EGF and SCR domains from the LAM-1 molecule;

(3) the L domain from the LAM-1 plus EGF and SCR domains from the CD62 molecule of the same family of proteins;

(4) the L plus EGF domains from LAM-1 (SCR from CD62; and (5) the L plus SCR domains from LAM-1 (EGF from CD62).

These cDNAs were transfected into cells which then produced the corresponding proteins. The pattern of reactivity of the various monoclonal antibodies was then determined as shown in Table 6, and the domain necessary for monoclonal antibody reactivity was assigned. For example, anti-LAM1-3 bound to cells expressing all the domains described with medium to very strong strength. Anti-LAM1-1, however, did not bind to cells which contained LAM-1 (L+SCR) or LAM-1 (L) alone. The epitope which is recognized by anti-LAM1-1 must, therefore, be composed of a site within the EGF domain, or which contains part of the L and EGF domains, but not the SCR domain. LAM1-3, on the other hand, must only contain the LAM-1(L) domain. The two antibodies are, therefore, distinguishable.

TABLE 5

| | Characteristics of Anti-LAM-1 Monoclonal Antibodies | | | | |
|---|---|---|---|---|---|
| Line | | | Antibody | | |
| 1 | | TQ1 | LAM1-1 | LAM1-2 | LAM1-3 |
| 2 | Isotype | G1 | G1 | M | G1 |
| 3 | Fluoresc.[1] | ++[7] | +++[7] | ++ | ++++[7] |
| 4 | HEV Bind[2] | N | B | wB | B |
| 5 | PPME Bind[3] | B | E | B | B |
| 6 | PPME Blocks[4] | −[7] | +/− | +/− | − |
| | Ability to Block Binding of Labelled Monoclonal Antibody | | | | |
| 7 | TQ-1[5] | +++ | − | +++ | +++ |
| 8 | Leu 8[5] | − | ++ | − | +++ |
| 9 | LAM1-1[5] | − | +++ | − | − |
| 10 | LAM1-3[5] | +++ | − | +++ | +++ |
| 11 | Domain Map[6] | L | L + EGF | L | L |
| | Species Cross Reactivity | | | | |
| 12 | Rhesus | − | +++ | − | +[1] |
| 13 | Tamarin | − | +++ | ++ | −− |
| 14 | Cow | ND | +++ | ND | +++ |
| 15 | Rabbit | +++ | ND | ++ | ++++ |
| 16 | Sheep | − | − | − | +++ |
| 17 | Dog | − | − | − | +++ |
| 18 | Cat | − | − | − | +++ |
| 19 | Pig | ND | ND | ND | + |
| 20 | Goat | ND | ND | ND | +++ |
| 21 | Epitope | C | A | B | D |

[1]= Fluorescence intensity, human lymphocytes and peripheral mononuclear cells. Fluorescence intensity of staining in indirect immunofluorescence assays is given on a 4 − (+) scale where (−) indicates no specific reactivity and ( . . . ) indicates the highest level of activity.
[2]= Monoclonal antibody blocking, High Endothelial Venule binding.
[3]= Monoclonal antibody blocking, phosphomannan monoester fragments (PPME).
[4]= PPME blocking monoclonal antibody.
[5]= Ability to block binding of antibody.
[6]= Domain mapped.
Abbreviations
Bind = Binding
B = Blocks
wB = weakly Blocks
E = Enhances
ND = Not Done
L = Lectin
EGF = Epidermal Growth Factor-like
SCR = Short Consensus Repeats
N = No effect

TABLE 6

Structural domains identified by the anti-LAM-1 monoclonal antibody reactive with fusion proteins

| Test mAb | Whole LAM-1 | Lectin | Lectin EGF | Lectin EGF SCRs | Lectin SCRs |
|---|---|---|---|---|---|
| anti-LAM1-1 | +++ | — | +++ | +++ | — |
| anti-LAM1-2 | ND | ND | ND | ND | ND |
| anti-LAM1-3 | +++ | +++ | ++ | ++++ | ++ | a = Values represent the relative intensity of immuno-fluorescence staining of COS-7 cells transfected with the LAM-1 cDNA or recombinant cDNAs encoding the lectin, EGF-like, or two SCR domains of LAM-1 with the rest of the cDNAS encoding CD62.
SCR = a domain of short consensus repeats.
EGF = epidermal growth factor-like domain.

REFERENCES

1. L. M. Stoolman et al., Cell 56: 907–910 (1989).
2. A. Duijvestijn et al., Immunol. Today 10: 23–28 (1989).
3. E. L. Berg et al., Immunol. Rev. 108: 5–18 (1989).
4. T. F. Tedder et al., J. Exp. Med. 170: 123–133 (1989).
5. T. F. Tedder et al., J. Immunol. 144: 532–540 (1989).
6. J. D. Griffith et al., J. Immunol. 145:576–584 (1990).
7. G. S. Kansas, J. Immunol. 134: 3003–3006 (1985).
8. E. L. Reinherz et al., J. Immunol. 1228: 463–468 (1982).
9. T. F. Tedder et al., Eur. J. Immunol. 20: 13511355 (1990).
10. M. E. Kanop et al., J. Immunol. 140: 3701–3706 (1988).
11. T. K. Kishimoto et al., Proc. Natl. Acad. Sci. 87: 2244–2248 (1990).
12. D. C. Ord et al., J. Biol. Chem. 14: 7760–7767 (1990).
13. L. Weiss et al., FASB J. 2: 1214 21 (1988).
14. B. T. Sher et al., Adv. Can. Res. 51: 361–389 (1988).
15. G. E. Rice et al., Science 246: 12303–1306 (1989).
16. R. F. Bargatze et &L., J. Exp. Med. 166:1125–1131 (12987).
17. L. M. Stoolman et al., J. Clin. Invest. 84: 1196–1205 (1989).
18. T. F. Tedder et al., Eur. J. Immunol. 16: 15391543 (1986).
19. F. Sanchez-Madrid et al., Proc. Natl. Acad. Sci. 79: 7489–7483 (1982).
20. R. Rothlein et al., J. Immunol. 137: 1270–1274 (1986).
21. G. S. Kansas et al., J. Immunol. 142: 3050–3057 (1989).
22. N. Dana et al., J. Immunol. 137: 3259–3263 (1986).
23. T. A. Yednock et al., J. Cell Biol. (1987).
24. T. A. Yednock et al., J. Cell Biol. 104: 725–731 (1987).
25. H. B. Stamper et al., J. Exp. Med. 144: 828–833 (1976)
26. E. C. Butcher et al., J. Immunol. 134: 2829 (1979).
27. T. F. Tedder et al., Molecular Immunol. 25: 1321–1330 (1988).
28. S. Jalkanen et al., Eur. J. Immunol. 16: 11951202 (1986).
29. S. Jalkanen et al., J. Cell Biol. 105: 893–990 (1987).
30. T. F. Tedder et al., J. Immunol. 134: 2989–2994 (1985).
31. H. Hidaka et al., Biochemistry 23: 5036–5040 (1984).
32. T. Tamaoki et al., Biochem. Biophys. Res. Commun. 135: 397–402 (1986).
33. T. K. Kishimoto et al., Science 245: 1238–1241 (1989).
34. T. M. Jung et al., J. Immunol. 144: 130–3136 (1990).
35. S. A. Michie et al., Am. J. Clin. Pathol. 88: 486–490 (1987).
36. A. Carbone et al., J. Pathol. 154: 133–140 (1988).
37. J. G. Strickler et al., Hum. Pathol. 19: 550–554 (1988).
38. G. S. Kansas et al., J. Immunol. 142: 3058–3062 (1989).
39. K. Miyake et al., J. Exp. Med. 172: 69–75 (1990).
40. S. T. Pals at al., Blood, 73: 885–888 (1989).
41. S. Aizawa et al., Proc. Natl. Acad. Sci. 85: 3180–3183 (1988).
42. L. M. Stoolman et al., J. Cell Biol. 99: 1535–1540 (1984).
43. M. A. Jutila et al., J. Immunol. 143: 3318–3324 (1989).

GLOSSARY

Definitions and Abbreviations

Selectins=a recently described family of cellular adhesion/homing receptor molecules identified by cDNA cloning. Members of this family include the leukocyte adhesion molecule-1 (LAM-1) which is the human homolog of the mouse lymphocyte homing receptor (mLHR), the human granule-membrane protein (GMP-140, PADGEM, CD62) which is expressed on activated platelets and endothelial cells, and the human endothelial leukocyte adhesion molecule-1 (ELAM-1) expressed on activated endothelial cells. The name "selecting" has been suggested for this family because of the presence of the lectin domain and their role in selective cell trafficking.

LN=lymph node

PMA=phorbol 12-myristate 13-acetate

PKC=protein kinease C

LAM-1=leukocyte adhesion molecule-1

CLL=chronic lymphocytic leukemia
NHL=non-Hodgkin's lymphoma
PPME=poly-phosphomonoester from the yeast HANSENULA cell wall
AML=acute myelogenous leukemia
CML=chronic myelogenous leukemia
PBMC=peripheral blood mononuclear cells
BM=bone marrow RPMI Medium=commercial product available from Gibco, Walkersville, Md.
FSC=follicular small cleaved cell lymphoma
CSF=colony stimulating factor
DSC=diffuse small cleaved cell lymphoma
FITC=fluorescein isothiocyanate
LPS=lipopolysaccharide
kb=kilobase

SEQUENCE LISTING ( 1 ) GENERAL INFORMATION:

( i i i ) NUMBER OF SEQUENCES: 1

( 2 ) INFORMATION FOR SEQ ID NO:1:

( i ) SEQUENCE CHARACTERISTICS:
      ( A ) LENGTH: 2330 base pairs
      ( B ) TYPE: nucleic acid
      ( C ) STRANDEDNESS: single
      ( D ) TOPOLOGY: linear ( i i ) MOLECULE TYPE: cDNA ( i i i ) HYPOTHETICAL: NO ( i v ) ANTI-SENSE: NO ( i x ) FEATURE:
      ( A ) NAME/KEY: CDS
      ( B ) LOCATION: 53..1210

( x i ) SEQUENCE DESCRIPTION: SEQ ID NO:1:

```
GAATTCCCTT  TGGGCAAGGA  CCTGAGACCC  TTGTGCTAAG  TCAAGAGGCT  CA ATG                      55
                                                              Met
                                                               1

GGC  TGC  AGA  AGA  ACT  AGA  GAA  GGA  CCA  AGC  AAA  GCC  ATG  ATA  TTT  CCA         103
Gly  Cys  Arg  Arg  Thr  Arg  Glu  Gly  Pro  Ser  Lys  Ala  Met  Ile  Phe  Pro
               5                        10                       15

TGG  AAA  TGT  CAG  AGC  ACC  CAG  AGG  GAC  TTA  TGG  AAC  ATC  TTC  AAG  TTG         151
Trp  Lys  Cys  Gln  Ser  Thr  Gln  Arg  Asp  Leu  Trp  Asn  Ile  Phe  Lys  Leu
          20                        25                       30

TGG  GGG  TGG  ACA  ATG  CTC  TGT  TGT  GAT  TTC  CTG  GCA  CAT  CAT  GGA  ACC         199
Trp  Gly  Trp  Thr  Met  Leu  Cys  Cys  Asp  Phe  Leu  Ala  His  His  Gly  Thr
     35                        40                       45

GAC  TGC  TGG  ACT  TAC  CAT  TAT  TCT  GAA  AAA  CCC  ATG  AAC  TGG  CAA  AGG         247
Asp  Cys  Trp  Thr  Tyr  His  Tyr  Ser  Glu  Lys  Pro  Met  Asn  Trp  Gln  Arg
50                       55                       60                       65

GCT  AGA  AGA  TTC  TGC  CGA  GAC  AAT  TAC  ACA  GAT  TTA  GTT  GCC  ATA  CAA         295
Ala  Arg  Arg  Phe  Cys  Arg  Asp  Asn  Tyr  Thr  Asp  Leu  Val  Ala  Ile  Gln
                    70                       75                       80

AAC  AAG  GCG  GAA  ATT  GAG  TAT  CTG  GAG  AAG  ACT  CTG  CCT  TTC  AGT  CGT         343
Asn  Lys  Ala  Glu  Ile  Glu  Tyr  Leu  Glu  Lys  Thr  Leu  Pro  Phe  Ser  Arg
               85                       90                       95

TCT  TAC  TAC  TGG  ATA  GGA  ATC  CGG  AAG  ATA  GGA  GGA  ATA  TGG  ACG  TGG         391
Ser  Tyr  Tyr  Trp  Ile  Gly  Ile  Arg  Lys  Ile  Gly  Gly  Ile  Trp  Thr  Trp
          100                       105                      110

GTG  GGA  ACC  AAC  AAA  TCT  CTC  ACT  GAA  GAA  GCA  GAG  AAC  TGG  GGA  GAT         439
Val  Gly  Thr  Asn  Lys  Ser  Leu  Thr  Glu  Glu  Ala  Glu  Asn  Trp  Gly  Asp
     115                       120                      125

GGT  GAG  CCC  AAC  AAC  AAG  AAG  AAC  AAG  GAG  GAC  TGC  GTG  GAG  ATC  TAT         487
Gly  Glu  Pro  Asn  Asn  Lys  Lys  Asn  Lys  Glu  Asp  Cys  Val  Glu  Ile  Tyr
130                      135                      140                      145
```

```
ATC AAG AGA AAC AAA GAT GCA GGC AAA TGG AAC GAT GAC GCC TGC CAC          535
Ile Lys Arg Asn Lys Asp Ala Gly Lys Trp Asn Asp Asp Ala Cys His
            150                 155                 160

AAA CTA AAG GCA GCC CTC TGT TAC ACA GCT TCT TGC CAG CCC TGG TCA          583
Lys Leu Lys Ala Ala Leu Cys Tyr Thr Ala Ser Cys Gln Pro Trp Ser
            165                 170                 175

TGC AGT GGC CAT GGA GAA TGT GTA GAA ATC ATC AAT AAT TAC ACC TGC          631
Cys Ser Gly His Gly Glu Cys Val Glu Ile Ile Asn Asn Tyr Thr Cys
            180                 185                 190

AAC TGT GAT GTG GGG TAC TAT GGG CCC CAG TGT CAG TTT GTG ATT CAG          679
Asn Cys Asp Val Gly Tyr Tyr Gly Pro Gln Cys Gln Phe Val Ile Gln
            195                 200                 205

TGT GAG CCT TTG GAG GCC CCA GAG CTG GGT ACC ATG GAC TGT ACT CAC          727
Cys Glu Pro Leu Glu Ala Pro Glu Leu Gly Thr Met Asp Cys Thr His
210                 215                 220                 225

CCT TTG GGA AAC TTC AAC TTC AAC TCA CAG TGT GCC TTC AGC TGC TCT          775
Pro Leu Gly Asn Phe Asn Phe Asn Ser Gln Cys Ala Phe Ser Cys Ser
                230                 235                 240

GAA GGA ACA AAC TTA ACT GGG ATT GAA GAA ACC ACC TGT GAA CCA TTT          823
Glu Gly Thr Asn Leu Thr Gly Ile Glu Glu Thr Thr Cys Glu Pro Phe
            245                 250                 255

GGA AAC TGG TCA TCT CCA GAA CCA ACC TGT CAA GTG ATT CAG TGT GAG          871
Gly Asn Trp Ser Ser Pro Glu Pro Thr Cys Gln Val Ile Gln Cys Glu
            260                 265                 270

CCT CTA TCA GCA CCA GAT TTG GGG ATC ATG AAC TGT AGC CAT CCC CTG          919
Pro Leu Ser Ala Pro Asp Leu Gly Ile Met Asn Cys Ser His Pro Leu
            275                 280                 285

GCC AGC TTC AGC TTT ACC TCT GCA TGT ACC TTC ATC TGC TCA GAA GGA          967
Ala Ser Phe Ser Phe Thr Ser Ala Cys Thr Phe Ile Cys Ser Glu Gly
290                 295                 300                 305

ACT GAG TTA ATT GGG AAG AAG AAA ACC ATT TGT GAA TCA TCT GGA ATC         1015
Thr Glu Leu Ile Gly Lys Lys Lys Thr Ile Cys Glu Ser Ser Gly Ile
            310                 315                 320

TGG TCA AAT CCT AGT CCA ATA TGT CAA AAA TTG GAC AAA AGT TTC TCA         1063
Trp Ser Asn Pro Ser Pro Ile Cys Gln Lys Leu Asp Lys Ser Phe Ser
            325                 330                 335

ATG ATT AAG GAG GGT GAT TAT AAC CCC CTC TTC ATT CCA GTG GCA GTC         1111
Met Ile Lys Glu Gly Asp Tyr Asn Pro Leu Phe Ile Pro Val Ala Val
            340                 345                 350

ATG GTT ACT GCA TTC TCT GGG TTG GCA TTT ATC ATT TGG CTG GCA AGG         1159
Met Val Thr Ala Phe Ser Gly Leu Ala Phe Ile Ile Trp Leu Ala Arg
355                 360                 365

AGA TTA AAA AAA GGC AAG AAA TCC AAG AGA AGT ATG AAT GAC CCA TAT         1207
Arg Leu Lys Lys Gly Lys Lys Ser Lys Arg Ser Met Asn Asp Pro Tyr
370                 375                 380                 385

TAAATCGCCC TTGGTGAAAG AAAATTCTTG AATACTAAA AATCATGAGA TCCTTTAAAT         1267

CCTTCCATGA AACGTTTTGT GTGGTGGCAC CTCCTACGTC AAACATGAAG TGTGTTTCCT         1327

TCAGTGCATC TGGGAAGATT CTACCTGAC CAACAGTTCC TTCAGCTTCC ATTTCACCCC         1387

TCATTTATCC CTCAACCCCC AGCCCACAGG TGTTTATACA GCTCAGCTTT TTGTCTTTTC         1447

TGAGGAGAAA CAAATAAGAC CATAAAGGGA AAGGATTCAT GTGGAATATA AAGATGGCTG         1507

ACTTGCTCT TTCTTGACTC TTGTTTTCAG TTTCAATTCA GTGCTGTACT TGATGACAGA         1567

CACTTCTAAA TGAAGTGCAA ATTGATACA TATGTGAATA TGGACTCAGT TTTCTTGCAG         1627

ATCAAATTTC GCGTCGTCTT CTGTATACGT GGAGGTACAC TCTATGAAGT CAAAAGTCTA         1687

CGCTCTCCTT TCTTTCTAAC TCCAGTGAAG TAATGGGGTC CTGCTCAAGT TGAAAGAGTC         1747

CTATTTGCAC TGTAGCCTCG CCGTCTGTGA ATTGGACCAT CCTATTTAAC TGGCTTCAGC         1807
```

| | | | | | | |
|---|---|---|---|---|---|---|
|CTCCCCACCT|TCTTCAGCCA|CCTCTCTTTT|TCAGTTGGCT|GACTTCCACA|CCTAGCATCT|1867|
|CATGAGTGCC|AAGCAAAAGG|AGAGAAGAGA|GAAATAGCCT|GCGCTGTTTT|TTAGTTTGGG|1927|
|GGTTTTGCTG|TTTCCTTTTA|TGAGACCCAT|TCCTATTTCT|TATAGTCAAT|GTTTCTTTTA|1987|
|TCACGATATT|ATTAGTAAGA|AAACATCACT|GAAATGCTAG|CTGCAACTGA|CATCTCTTTG|2047|
|ATGTCATATG|GAAGAGTTAA|AACAGGTGGA|GAAATTCCTT|GATTCACAAT|GAAATGCTCT|2107|
|CCTTTCCCCT|GCCCCAGAC|CTTTTATCCA|CTTACCTAGA|TTCTACATAT|TCTTTAAATT|2167|
|TCATCTCAGG|CCTCCCTCAA|CCCCACCACT|TCTTTTATAA|CTAGTCCTTT|ACTAATCCAA|2227|
|CCCATGATGA|GCTCCTCTTC|CTGGCTTCTT|ACTGAAAGGT|TACCCTGTAA|CATGCAATTT|2287|
|TGCATTTGAA|TAAAGCCTGC|TTTTAAGTG|TTAAAAAGAA|TTC| |2330|

We claim:

1. A hybridoma cell line which has American Type Culture Collection Deposit No. HB 10771 and produces anti-LAM1-3 monoclonal antibody.

2. An anti-LAM1-3 monoclonal antibody produced by the hybridoma cell line which has American Type Culture Collection Deposit No. HB 10771.

3. A chimeric antibody comprising the variable region of the anti-LAM1-3 antibody according to claim 2 and a constant region derived from a human monoclonal antibody.

4. The monoclonal antibody according to claim 2, which is detectably labelled.

5. A monoclonal antibody according to claim 4, wherein the detectable label is selected from the group consisting of radioisotopes or fluorescent markers.

* * * * *